(12) United States Patent
Snyder et al.

(10) Patent No.: US 9,101,590 B2
(45) Date of Patent: Aug. 11, 2015

(54) DEFINED CULTURE CONDITIONS OF HUMAN EMBRYONIC STEM CELLS

(75) Inventors: Michael P. Snyder, Fairfield, CT (US); Joyce J. Lu, New Haven, CT (US)

(73) Assignee: Yale University, New Haven, CT (US)

( * ) Notice: Subject to any disclaimer, the term of this patent is extended or adjusted under 35 U.S.C. 154(b) by 2115 days.

(21) Appl. No.: 11/989,363

(22) PCT Filed: Jul. 28, 2006

(86) PCT No.: PCT/US2006/029473
§ 371 (c)(1),
(2), (4) Date: Jan. 24, 2008

(87) PCT Pub. No.: WO2007/016366
PCT Pub. Date: Feb. 8, 2007

(65) Prior Publication Data
US 2011/0076253 A1    Mar. 31, 2011

Related U.S. Application Data

(60) Provisional application No. 60/704,088, filed on Jul. 29, 2005, provisional application No. 60/773,572, filed on Feb. 15, 2006.

(51) Int. Cl.
*A61K 38/18* (2006.01)
*A61K 38/19* (2006.01)
*A61K 38/28* (2006.01)
*A61K 38/40* (2006.01)

(52) U.S. Cl.
CPC .......... *A61K 38/191* (2013.01); *A61K 38/1825* (2013.01); *A61K 38/28* (2013.01); *A61K 38/40* (2013.01)

(58) Field of Classification Search
CPC .......... A61K 2300/00; A61K 38/1825; A61K 35/28; A61K 35/44; A61K 35/50; A61K 35/51; A61K 35/12; A61K 45/00; A61K 8/982; A61K 38/00; A61K 38/191; A61K 38/28; A61K 38/40; A61K 48/00; C12N 2506/02; C12N 15/85

See application file for complete search history.

(56) References Cited

U.S. PATENT DOCUMENTS

| | | | |
|---|---|---|---|
| 6,713,057 B1 | 3/2004 | Chatterjee | |
| 6,800,480 B1 | 10/2004 | Bodnar et al. | |
| 7,005,252 B1 | 2/2006 | Thomson | |
| 7,445,931 B2 * | 11/2008 | Condie et al. | 435/377 |
| 2004/0110286 A1 * | 6/2004 | Bhatia | 435/366 |
| 2004/0219136 A1 | 11/2004 | Hariri | |
| 2004/0244806 A1 | 12/2004 | Ferree | |
| 2005/0233446 A1 | 10/2005 | Parsons et al. | |
| 2006/0051862 A1 | 3/2006 | Amit et al. | |
| 2006/0127370 A1 | 6/2006 | Niwa et al. | |

FOREIGN PATENT DOCUMENTS

WO    WO 03/104442    12/2003

OTHER PUBLICATIONS

Liu, et al. 2000, "Hypoxic Preconditioning Protects Cultured Neurons against Hypoxic stress via TNF-.alpha.and Ceramide", Am. J. Physiol. Cell Physiol., 278:C144-C153.*
Amit et al., 2004, Biol. Reprod. 70: 837-845.
Pera, 2005, Nat. Methods 2: 164-165.
Sato et al., 2004, Nat. Med. 10: 55-63.
Dravid et al., 2005, Stem Cells 23: 1489-1501.
Ludwig et al., 2006, Nat. Biotechnol. 24: 185-187.

* cited by examiner

*Primary Examiner* — Debbie K Ware
(74) *Attorney, Agent, or Firm* — Saul Ewing, LLP; Kathryn Doyle

(57) ABSTRACT

The present invention relates to compositions and methods for culturing stem cells, particularly embryonic stem cells. Specifically, the invention relates to a culture medium that supports proliferation of substantially undifferentiated stem cells, while maintaining potency of the cells. An an embodiment, the culture medium is defined and supports proliferation of substantially undifferentiated embryonic stem cells in essentially serum free and feeder cell free conditions. Compositions for making the medium and methods using the culture medium are also provided.

11 Claims, 6 Drawing Sheets

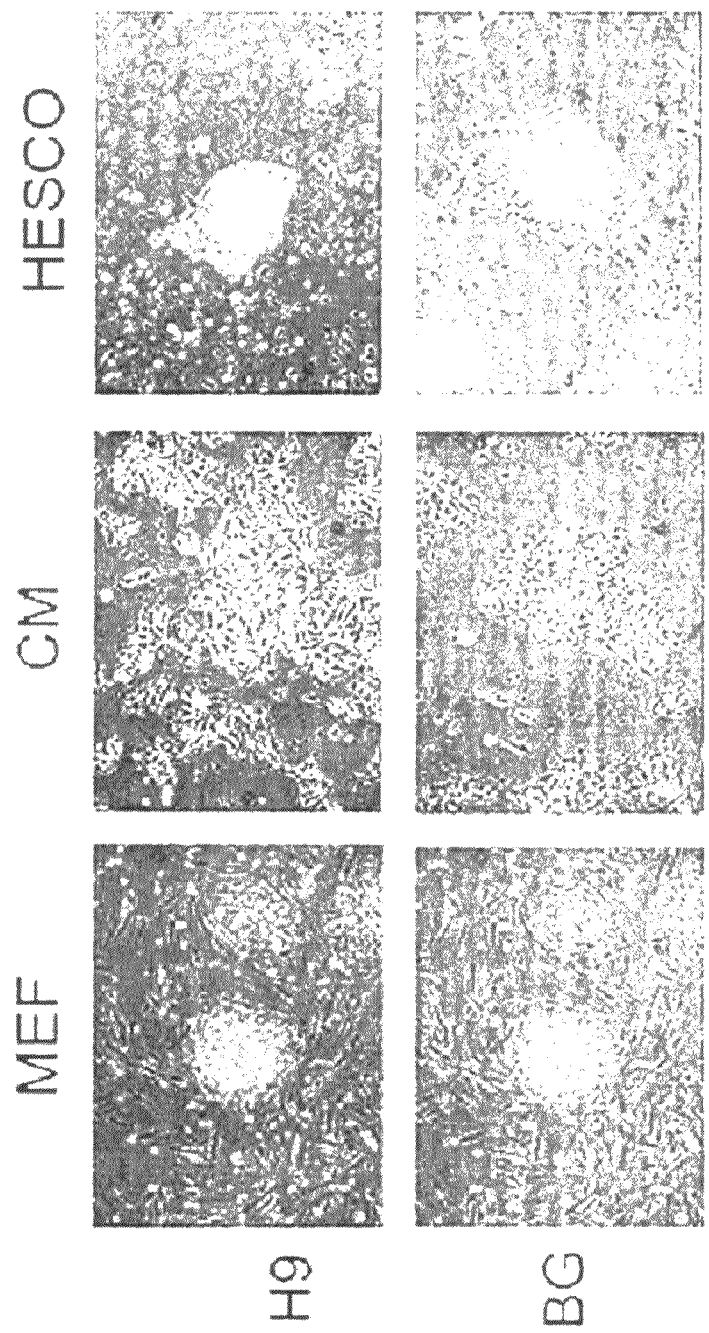

FIGURE 3
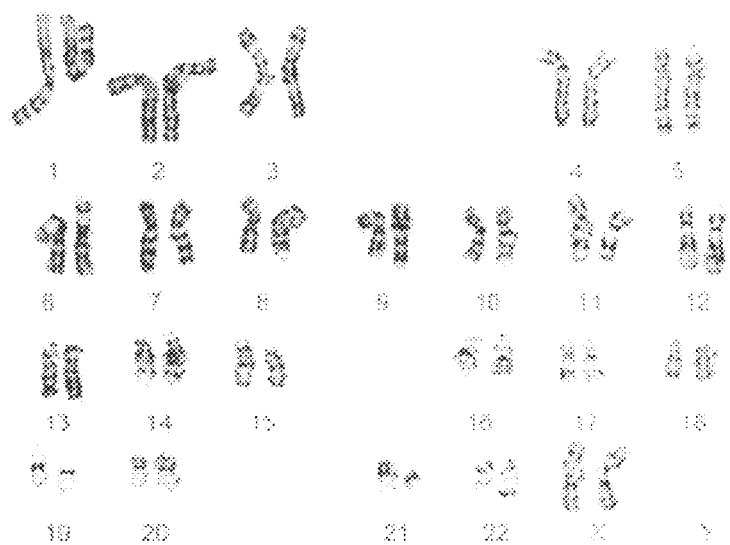
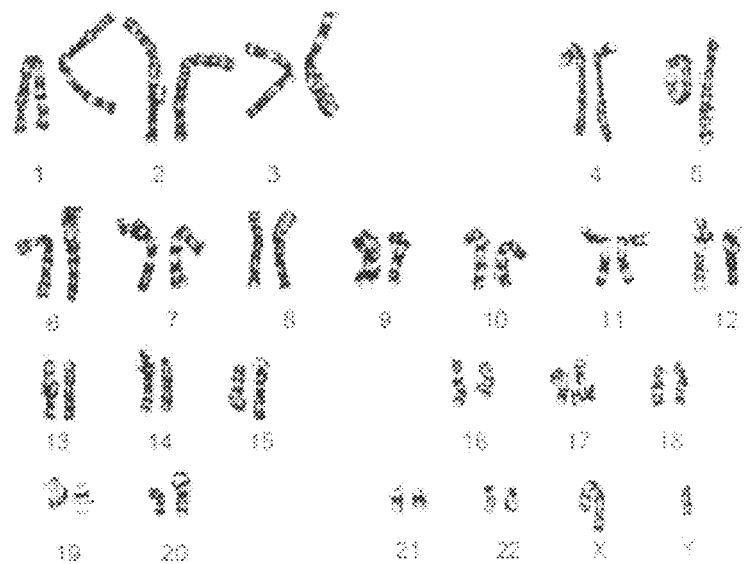

SEQUENCE LISTING

```
<160> NUMBER OF SEQ ID NOS: 6

<210> SEQ ID NO 1
<211> LENGTH: 201
<212> TYPE: PRT
<213> ORGANISM: Homo sapiens
<220> FEATURE:
<221> NAME/KEY: MISC_FEATURE
<222> LOCATION: (1)..(201)
<223> OTHER INFORMATION: Extracellular portion

<400> SEQUENCE: 1

Thr Gln Gln Thr Glu Leu Gln Ser Leu Arg Arg Glu Val Ser Arg Leu
1               5                   10                  15

Gln Gly Thr Gly Gly Pro Ser Gln Asn Gly Glu Gly Tyr Pro Trp Gln
            20                  25                  30

Ser Leu Pro Glu Gln Ser Ser Asp Ala Leu Glu Ala Trp Glu Asn Gly
        35                  40                  45

Glu Arg Ser Arg Lys Arg Arg Ala Val Leu Thr Gln Lys Gln Lys Lys
    50                  55                  60

Gln His Ser Val Leu His Leu Val Pro Ile Asn Ala Thr Ser Lys Asp
65                  70                  75                  80

Asp Ser Asp Val Thr Glu Val Met Trp Gln Pro Ala Leu Arg Arg Gly
                85                  90                  95

Arg Gly Leu Gln Ala Gln Gly Tyr Gly Val Arg Ile Gln Asp Ala Gly
            100                 105                 110

Val Tyr Leu Leu Tyr Ser Gln Val Leu Phe Gln Asp Val Thr Phe Thr
        115                 120                 125
```

```
Met Gly Gln Val Val Ser Arg Glu Gly Gln Gly Arg Gln Glu Thr Leu
    130                 135                 140

Phe Arg Cys Ile Arg Ser Met Pro Ser His Pro Asp Arg Ala Tyr Asn
145                 150                 155                 160

Ser Cys Tyr Ser Ala Gly Val Phe His Leu His Gln Gly Asp Ile Leu
                165                 170                 175

Ser Val Ile Ile Pro Arg Ala Arg Ala Lys Leu Asn Leu Ser Pro His
                180                 185                 190

Gly Thr Phe Leu Gly Phe Val Lys Leu
                195                 200

<210> SEQ ID NO 2
<211> LENGTH: 603
<212> TYPE: DNA
<213> ORGANISM: Homo sapiens
<220> FEATURE:
<221> NAME/KEY: misc_feature
<222> LOCATION: (1)..(603)
<223> OTHER INFORMATION: Coding sequence for extracellular portion

<400> SEQUENCE: 2
acccaacaaa cagagctgca gagcctcagg agagaggtga gccggctgca ggggacagga      60
ggcccctccc agaatgggga agggtatccc tggcagagtc tcccggagca gagttccgat     120
gccctggaag cctgggagaa tggggagaga tcccggaaaa ggagagcagt gctcacccaa     180
aaacagaaga agcagcactc tgtcctgcac ctggttccca ttaacgccac ctccaaggat     240
gactccgatg tgacagaggt gatgtggcaa ccagctctta gcgtgggag aggcctacag     300 gcccaaggat atggtgtccg aatccaggat gctggagttt atctgctgta tagccaggtc     360
ctgtttcaag acgtgacttt caccatgggg caggtggtgt ctcgagaagg ccaaggaagg     420
caggagactc tattccgatg tataagaagt atgccctccc acccggaccg ggcctacaac     480
agctgctata gcgcaggtgt cttccattta caccaagggg atattctgag tgtcataatt     540
ccccgggcaa gggcgaaact taacctctct ccacatggaa ccttcctggg gtttgtgaaa     600
ctg                                                                   603

<210> SEQ ID NO 3
<211> LENGTH: 203
<212> TYPE: PRT
<213> ORGANISM: Homo sapiens
<220> FEATURE:
<221> NAME/KEY: MISC_FEATURE
<222> LOCATION: (1)..(203)
<223> OTHER INFORMATION: Extracellular portion

<400> SEQUENCE: 3

Leu Gln Gly His His Ala Glu Lys Leu Pro Ala Gly Ala Gly Ala Pro
1               5                   10                  15

Lys Ala Gly Leu Glu Glu Ala Pro Ala Val Thr Ala Gly Leu Lys Ile
                20                  25                  30

Phe Glu Pro Pro Ala Pro Gly Glu Gly Asn Ser Ser Gln Asn Ser Arg
            35                  40                  45

Asn Lys Arg Ala Val Gln Gly Pro Glu Glu Thr Val Thr Gln Asp Cys
        50                  55                  60

Leu Gln Leu Ile Ala Asp Ser Glu Thr Pro Thr Ile Gln Lys Gly Ser
65                  70                  75                  80

Tyr Thr Phe Val Pro Trp Leu Leu Ser Phe Lys Arg Gly Ser Ala Leu
                85                  90                  95
```

```
Glu Glu Lys Glu Asn Lys Ile Leu Val Lys Glu Thr Gly Tyr Phe Phe
            100                 105                 110

Ile Tyr Gly Gln Val Leu Tyr Thr Asp Lys Thr Tyr Ala Met Gly His
        115                 120                 125

Leu Ile Gln Arg Lys Lys Val His Val Phe Gly Asp Glu Leu Ser Leu
    130                 135                 140

Val Thr Leu Phe Arg Cys Ile Gln Asn Met Pro Glu Thr Leu Pro Asn
145                 150                 155                 160

Asn Ser Cys Tyr Ser Ala Gly Ile Ala Lys Leu Glu Glu Gly Asp Glu
                165                 170                 175

Leu Gln Leu Ala Ile Pro Arg Glu Asn Ala Gln Ile Ser Leu Asp Gly
            180                 185                 190

Asp Val Thr Phe Phe Gly Ala Leu Lys Leu Leu
            195                 200
```

```
<210> SEQ ID NO 4
<211> LENGTH: 609
<212> TYPE: DNA
<213> ORGANISM: Homo sapiens
<220> FEATURE:
<221> NAME/KEY: misc_feature
<222> LOCATION: (1)..(609)
<223> OTHER INFORMATION: Sequence coding for extracellular portion
<220> FEATURE:
<221> NAME/KEY: misc_feature
<222> LOCATION: (1)..(609)
<223> OTHER INFORMATION: Coding sequence for extracellular portion

<400> SEQUENCE: 4
ctgcagggcc accacgcgga gaagctgcca gcaggagcag gagcccccaa ggccggcctg      60
gaggaagctc cagctgtcac cgcgggactg aaaatctttg aaccaccagc tccaggagaa     120
ggcaactcca gtcagaacag cagaaataag cgtgccgttc agggtccaga gaaacagtc     180 actcaagact gcttgcaact gattgcagac agtgaaacac caactataca aaaggatct    240 tacacatttg ttccatggct tctcagcttt aaaaggggaa gtgccctaga agaaaaagag    300 aataaaaatat tggtcaaaga aactggttac tttttttatat atggtcaggt tttatatact   360
gataagacct acgccatggg acatctaatt cagaggaaga aggtccatgt ctttggggat    420
gaattgagtc tggtgacttt gtttcgatgt attcaaaata tgcctgaaac actacccaat   480
aattcctgct attcagctgg cattgcaaaa ctggaagaag gagatgaact ccaacttgca    540
ataccaagag aaaatgcaca aatatcactg gatggagatg tcacatttttt tggtgcattg    600 aaactgctg                                                             609
```

```
<210> SEQ ID NO 5
<211> LENGTH: 352
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(352)

<400> SEQUENCE: 5

Met Ala Pro Leu Gly Tyr Phe Leu Leu Leu Cys Ser Leu Lys Gln Ala
                -20                 -15                 -10

Leu Gly Ser Tyr Pro Ile Trp Trp Ser Leu Ala Val Gly Pro Gln Tyr
            -5                  -1   1                  5
```

| | | | | | | | | | | | |
|---|---|---|---|---|---|---|---|---|---|---|---|
|Ser|Ser|Leu|Gly|Ser|Gln|Pro|Ile|Leu|Cys|Ala|Ser|Ile|Pro|Gly|Leu
| | |10| | |15| | |20| | | |

Ser Ser Leu Gly Ser Gln Pro Ile Leu Cys Ala Ser Ile Pro Gly Leu
 10              15              20

Val Pro Lys Gln Leu Arg Phe Cys Arg Asn Tyr Val Glu Ile Met Pro
 25              30              35              40

Ser Val Ala Glu Gly Ile Lys Ile Gly Ile Gln Glu Cys Gln His Gln
             45              50              55

Phe Arg Gly Arg Arg Trp Asn Cys Thr Thr Val His Asp Ser Leu Ala
             60              65              70

Ile Phe Gly Pro Val Leu Asp Lys Ala Thr Arg Glu Ser Ala Phe Val
         75              80              85

His Ala Ile Ala Ser Ala Gly Val Ala Phe Ala Val Thr Arg Ser Cys
         90              95             100

Ala Glu Gly Thr Ala Ala Ile Cys Gly Cys Ser Ser Arg His Gln Gly
105             110             115             120

Ser Pro Gly Lys Gly Trp Lys Trp Gly Gly Cys Ser Glu Asp Ile Glu
                125             130             135

Phe Gly Gly Met Val Ser Arg Glu Phe Ala Asp Ala Arg Glu Asn Arg
             140             145             150

Pro Asp Ala Arg Ser Ala Met Asn Arg His Asn Asn Glu Ala Gly Arg
             155             160             165

Gln Ala Ile Ala Ser His Met His Leu Lys Cys Lys Cys His Gly Leu
         170             175             180

Ser Gly Ser Cys Glu Val Lys Thr Cys Trp Trp Ser Gln Pro Asp Phe
185             190             195             200

Arg Ala Ile Gly Asp Phe Leu Lys Asp Lys Tyr Asp Ser Ala Ser Glu
                205             210             215

Met Val Val Glu Lys His Arg Glu Ser Arg Gly Trp Val Glu Thr Leu
             220             225             230

Arg Pro Arg Tyr Thr Tyr Phe Lys Val Pro Thr Glu Arg Asp Leu Val
             235             240             245

Tyr Tyr Glu Ala Ser Pro Asn Phe Cys Glu Pro Asn Pro Glu Thr Gly
    250             255             260

Ser Phe Gly Thr Arg Asp Arg Thr Cys Asn Val Ser Ser His Gly Ile
265             270             275             280

Asp Gly Cys Asp Leu Leu Cys Cys Gly Arg Gly His Asn Ala Arg Ala
                285             290             295

Glu Arg Arg Arg Glu Lys Cys Arg Cys Val Phe His Trp Cys Cys Tyr
                300             305             310

Val Ser Cys Gln Glu Cys Thr Arg Val Tyr Asp Val His Thr Cys Lys
        315             320             325

<210> SEQ ID NO 6
<211> LENGTH: 1056
<212> TYPE: DNA
<213> ORGANISM: Homo sapiens

<400> SEQUENCE: 6
atggccccac tcggatactt cttactcctc tgcagcctga agcaggctct gggcagctac      60
ccgatctggt ggtcgctggc tgttgggcca cagtattcct ccctgggctc gcagcccatc     120
ctgtgtgcca gcatcccggg cctggtcccc aagcagctcc gcttctgcag gaactacgtg     180
gagatcatgc cagcgtggc cgagggcatc aagattggca tccaggagtg ccagcaccag     240
ttccgcggcc gccggtggaa ctgcaccacc gtccacgaca gcctggccat cttcgggccc     300

-continued

```
gtgctggaca aagctaccag ggagtcggcc tttgtccacg ccattgcctc agccggtgtg    360
gcctttgcag tgacacgctc atgtgcagaa ggcacggccg ccatctgtgg ctgcagcagc    420
cgccaccagg gctcaccagg caagggctgg aagtggggtg gctgtagcga ggacatcgag    480
tttggtggga tggtgtctcg ggagttcgcc gacgcccggg agaaccggcc agatgcccgc    540
tcagccatga accgccacaa caacgaggct gggcgccagg ccatcgccag ccacatgcac    600
ctcaagtgca agtgccacgg gctgtcgggc agctgcgagg tgaagacatg ctggtggtcg    660
caacccgact tccgcgccat cggtgacttc ctcaaggaca agtacgacag cgcctcggag    720
atggtggtgg agaagcaccg ggagtcccgc ggctgggtgg agaccctgcg gccgcgctac    780
acctacttca aggtgcccac ggagcgcgac ctggtctact acgaggcctc gcccaacttc    840
tgcgagccca accctgagac gggctccttc ggcacgcgcg accgcacctg caacgtcagc    900
tcgcacggca tcgacggctg cgacctgctg tgctgcggcc gcggccacaa cgcgcgagcg    960
gagcggcgcc gggagaagtg ccgctgcgtg ttccactggt gctgctacgt cagctgccag   1020
gagtgcacgc gcgtctacga cgtgcacacc tgcaag                              1056
```

DEFINED CULTURE CONDITIONS OF HUMAN EMBRYONIC STEM CELLS

CROSS-REFERENCE TO RELATED APPLICATIONS

This is a National Stage application of PCT International Application No. PCT/US2006/029473, filed Jul. 28, 2006, which in turn claims the benefit pursuant to 35 U.S.C. §119(e) of U.S. Provisional Application Nos. 60/704,088and 60/773,572, filed on Jul. 29, 2005and Feb. 15, 2006, respectively, each of which is hereby incorporated by reference in its entirety herein.

STATEMENT REGARDING FEDERALLY SPONSORED RESEARCH OR DEVELOPMENT

This invention was supported in part by funds obtained from the U.S. Government (National Institutes of Health, Grant Number P50HG002357), and the U.S. Government therefore has certain rights in the invention.

BACKGROUND OF THE INVENTION

Human embryonic stem cells (hESCs) are pluripotent cells that have the potential to differentiate into the three germ layers and possibly all tissues of the human body (Strelchenko et al., 2004, Reprod Biomed Online 9: 623-9; D'Amour et al., 2000, Nat Biotechnol 18: 381-2; Keller et al., 1999, Nat Med 5: 151-2; Trounson, 2002, Reprod Biomed Online 4 Suppl 1: 58-63; Odorico et al., 2001, Stem Cells 19: 193-204; Gertow et al., 2004, Stem Cells Dev 13: 421-35). hESCs were originally isolated from the inner cell mass of human embryos and were found capable of passaging through over 100 divisions while maintaining pluripotency (Thomson et al., 1998, Curr Top Dev Biol 38: 133-65; Reubinoff et al., 2000, Nat Biotechnol 18: 399-404). In addition to protocols for culturing hESCs in an undifferentiated state, differentiation protocols for hESCs have been successfully established in vitro for many cell types, including neuronal cells (Park et al., 2005, J Neurochem 92: 1265-76), hematopoietic cells (Kaufman et al., 2002, J Anat 200: 243-8), insulin-producing cells (Assady et al., 2001, Diabetes 50: 1691-7), endothelial cells (Levenberg et al., 2002, Proc Natl Acad Sci USA 99: 4391-6), and cardiomyocytes (Mummery et al., 2002, J Anat 200: 233-42), among others (Odorico et al., 2001, Stem Cells 19: 193-204; Reubinoff et al., 2000, Nat Biotechnol 18: 399-404).

The ability of hESCs to differentiate into many cell types distinguishes them from adult stem cells, which can typically only differentiate into limited cell types (Thomson et al., 1998, Curr Top Dev Biol 38: 133-65; Reubinoff et al., 2000, Nat Biotechnol 18: 399-404). Thus, hESCs provide a particularly useful system for studies of development. hESCs also have enormous therapeutic potential for treatment of a wide variety of diseases, including Parkinson's disease, diabetes and heart failure, among others To make hESCs compatible for clinical therapy, banks of hESC lines with different human leukocyte antigens (HLA) are being established to enable HLA matches to reduce the likelihood of graft rejection by a transplant recipient (ISSCR, 2002, The ISSCR Newsletter-The Pulse Vol 1(3) Nov. 1, 2002; National Institutes of Health, 2005, "NIH Awards a National Stem Cell Bank and New Centers of Excellence in Translational Human Stem Cell Research" Oct. 3, 2005 Press Release; Taylor et al., 2005, Lancet 366: 2019-25). In addition, other technologies, such as nuclear transfer, may allow the generation of autologous embryonic stem cells in the future (Wakayama et al., 2001, Science 292: 740-3). Thus, hESCs are expected to provide a great resource for regenerative medicine (Dvash et al., 2004, Best Pract Res Clin Obstet Gynaecol 18: 929-40).

Until recently, hESC lines were derived and proliferated in culture medium containing animal products. The presence of xenograft or allograft animal products in hESC culture media has at least four problems (Pera, 2005, Nat. Methods 2:164-165; Draper et al., 2004, Stem Cells Dev. 13:325-336; Stojkovi et al., 2004, Reproduction 128:259-267). First, animal products may contain toxic proteins or immunogens that evoke an immune response in the recipient and thus lead to rejection upon transplantation (Martin et al., 2005, Nat Med 11: 228-32). Second, the use of animal products increases the risk of contamination by animal pathogens, such as viruses or prions, which could endanger the recipient (Cobo et al., 2005, Appl Microbiol Biotechnol 68: 456-66). Third, separating animal products, such as feeder cells, from hESCs is both time- and labor-intensive. Finally, the use of medium with undefined factors greatly complicates developmental studies, for instance, by undermining the predictability of culture conditions and possibly leading to undesirable cell differentiation. Therefore, there is a great need for a defined medium with animal products that supports growth of hESCs without substantial differentiation, and while maintaining pluripotency.

To date, four key components required for hESC culture have been identified. First, basic fibroblast growth factor (bFGF) has been shown to be essential for hESC self-renewal (Granerus et al., 1996, Cell Prolif 29: 309-14; Xu et al., 2005, Stem Cells 23: 315-23). Second, feeder cells, conditioned medium, or cytokines, such as transforming growth factor (TGF) (Beattie et al., 2005, Stem Cells 23: 489-95) or Wnt3 (Sato et al., 2004, Nat Med 10: 55-63), are necessary. Third, an extracellular matrix is necessary. Fourth, fetal bovine serum or serum replacement (Holden, 2005, Science 307: 1393; Xu et al., 2001, Nat Biotechnol 19: 971-4) is necessary.

Several types of matrices have been used to coat the culture dish surface for hESC culture. BD Matrigel™ (BD Biosciences, San Jose, Calif.), a preparation rich in multiple extracellular components, is secreted by mouse Engelbreth Holm-Swarm sarcoma cells and is able to support hESC growth (Xu et al., 2001, Nat Biotechnol 19: 971-4). Matrigel™ contains laminin, collagen type IV, heparan sulfate, proteoglycan, and entactin (Kleinman et al., 1986, Biochemistry 25: 312-8). Human serum can substitute for Matrigel™, thus avoiding a xeno component in hESC culture (Stojkovic et al., 2005, Stem Cells 23: 895-902). However, both Matrigel™ and human serum are mixtures with undefined components. Other defined matrices, such as fibronectin, laminin, and collagen, can support feeder-cell-free hESC growth, but the efficacy varies among laboratories, and some reagents have disparities among different lots (Xu et al., 2001, Nat. Biotechnol. 19: 971-4; Ludwig et al., 2006, Nat. Biotechnol. 24: 185-187; Li et al., 2005, Biotechnol. Bioeng. 91: 688-98).

Serum or serum replacement is also essential for hESC culture. Knockout™ SR (Invitrogen, Carlsbad, Calif.), which contains animal-derived products, is a serum replacement frequently used in hESC culture (Xu et al., 2005, Stem Cells 23: 315-23). An animal-free product, X-VIVO™ (Cambrex Bio Science, Walkersville, Md.) supports hESC growth, however it was optimized for hematopoietic cell culture (Li et al., 2005, Biotechnol Bioeng 91: 688-98). Disadvantageously, Knockout™ serum and X-VIVO™ are both proprietary materials and contain multiple components. Moreover, in feeder-cell-free culture, hESCs grown in medium containing these serum replacements form differentiated cells around the hESC colonies, indicating that optimal conditions have not been achieved (Li et al., 2005, Biotechnol Bioeng 91: 688-98).

Because of these problems with currently known culture media for hESC, there is a need for a better, defined culture medium with minimal components that reproducibly supports robust growth of hESCs. The present invention meets these needs.

SUMMARY OF THE INVENTION

The invention provides a culture medium for stem cells, wherein the medium comprises a basal medium, a protein comprising a member of the tumor necrosis factor (TNF) family, a protein comprising a member of the Wnt family, a protein comprising insulin, a protein comprising transferrin and a protein comprising fibroblast growth factor (FGF).

The invention further provides a culture system for culturing stem cells, the culture system comprising a culture medium and a matrix, wherein the culture medium comprises a basal medium, a protein comprising a member of the tumor necrosis factor (TNF) family, a protein comprising a member of the Wnt family, a protein comprising insulin, a protein comprising transferrin and a protein comprising fibroblast growth factor (FGF).

In some embodiments of the culture medium or culture system, the protein comprising a TNF member is selected from the group consisting of April, an April substitute, BAFF, a BAFF substitute and combinations thereof. In some embodiments, the FGF is basic fibroblast growth factor (bFGF). In some embodiments, the member of the Wnt family is Wnt3a or a Wnt3a substitute. In some embodiments, the medium or the composition further comprise at least one of a protein comprising albumin or cholesterol. In some embodiments, the cholesterol is chemically defined cholesterol. In some embodiments, the basal medium is selected from the group consisting of DMEM and DMEM/F12. In some embodiments, any of said proteins is recombinantly synthesized, chemically synthesized or isolated from a human biological sample. In some embodiments, the culture medium is essentially free of animal serum.

The invention further provides a composition for preparing a culture medium, the composition comprising a protein comprising a member of the tumor necrosis factor family and a protein comprising a member of the Wnt family.

In some embodiments of the composition, the protein comprising a TNF member is selected from the group consisting of April, an April substitute, BAFF, a BAFF substitute and combinations thereof. In some embodiments, the member of the Wnt family is Wnt3a or a Wnt3a substitute. In some embodiments, the medium or the composition further comprise at least one of a protein comprising insulin, a protein comprising transferrin, a protein comprising albumin, a protein comprising FGF, or cholesterol. In some embodiments, the FGF is basic fibroblast growth factor (bFGF). In some embodiments, any of the proteins are recombinantly synthesized, chemically synthesized or isolated from a human biological sample.

A composition useful for preparing a culture medium is also featured in the invention. The composition comprises a protein comprising a member of the tumor necrosis factor family, a protein comprising a member of the Wnt family, a protein comprising insulin, a protein comprising transferrin, a protein comprising albumin, cholesterol and a basal medium. In another embodiment, the composition comprises a protein comprising a member of the tumor necrosis factor family, a protein comprising insulin, a protein comprising transferrin, a protein comprising albumin, cholesterol and a basal medium.

The invention also features a composition of matter comprising stem cells and a culture medium, wherein the culture medium comprises a basal medium, a protein comprising a member of the tumor necrosis factor (TNF) family, a protein comprising a member of the Wnt family, a protein comprising insulin, a protein comprising transferrin and a protein comprising fibroblast growth factor (FGF).

In some embodiments of the composition of matter, the protein comprising a TNF member is selected from the group consisting of April, an April substitute, BAFF, a BAFF substitute and combinations thereof. In some embodiments, the member of the Wnt family is Wnt3a or a Wnt3a substitute. In some embodiments, the FGF is basic fibroblast growth factor (bFGF). In some embodiments, the composition further comprises cholesterol. In some embodiments, the cholesterol is chemically defined cholesterol. In some embodiments, the basal medium is selected from the group consisting of DMEM and DMEM/F12. In some embodiments, any of said proteins is recombinantly synthesized, chemically synthesized or isolated from a human biological sample. In some embodiments, the culture medium is essentially free of animal serum. In some embodiments, the stem cell is an embryonic stem cell. In some embodiments, the stem cell is a human embryonic stem cell.

The invention further provides a method of culturing a stem cell using a culture system of the invention. In some embodiments, the stem cell is an embryonic stem or a human embryonic stem cell. In some embodiments, the embryonic stem cell is cultured for at least about 4 passages and wherein the embryonic stem cell proliferates in a substantially undifferentiated state while maintaining the potential to differentiate into derivatives of endoderm, mesoderm and ectoderm tissues and while maintaining the karyotype of the embryonic stem cell.

The invention also provides a method of cell therapy, the method comprising: culturing stem cells in a defined culture medium to produce a population of isolated stem cells, and administering a therapeutically effective amount of said population of stem cells to a recipient in need of such cells, wherein the defined culture medium comprises a basal medium, a protein comprising a member of the Wnt family, a protein comprising FGF, a protein comprising insulin, a protein comprising transferrin, a protein comprising a member of the tumor necrosis factor (TNF) family, a protein comprising albumin and cholesterol, and wherein any of the proteins are recombinantly synthesized or chemically synthesized, and further wherein the culturing is essentially free of animal serum and feeder cells In some embodiments of the method of cell therapy, the stem cells are human embryonic stem cells. In other embodiments, the method further comprises inducing differentiation of said stem cells prior to administering them to said recipient.

The invention further features kits comprising compositions of the invention, useful for making a culture medium. Kits for maintaining and proliferating a stem cell in a culture medium are also provided.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a series of images depicting the morphology of hESCs cultured in the presence of feeder cells (mouse embryonic fibroblasts, MEF), conditioned medium (CM), or a defined culture medium of the invention (HESCO). Original magnification: X40.

FIG. 2, comprising FIG. 2A is a series of images depicting hESCs cultured in the presence of mouse embryonic fibroblast (MEF) feeder cells, conditioned medium (CM), or HESCO medium (HESCO) and assayed for alkaline phosphatase. Magnification: ×100. In FIG. 2B, the left column of images (Antibody) depicts hESCs immunofluorescence stained with antibodies to stem cell markers: Oct4, SSEA3, SSEA4, TRA-1-60 (Tra 60), TRA-1-81 (Tra 81), and control mouse IgM (Ig). The middle column of images (DAPI) depicts hESCs nuclei stained with DAPI. The right column of images (Merge) depicts the overlay of FITC antibody staining and DAPI signals. Original magnification: ×200.

FIG. 3, comprising FIGS. 3A and 3B, depicts chromosomes from hESCs cultured in HESCO to assess genetic stability. The karyotypes of H9 (FIG. 3A) and BG01 cells (FIG. 3B) cultured in HESCO for 11 passages and 8 passages, respectively, were analyzed using Giemsa staining.

DETAILED DESCRIPTION OF THE INVENTION

Figure 2A:
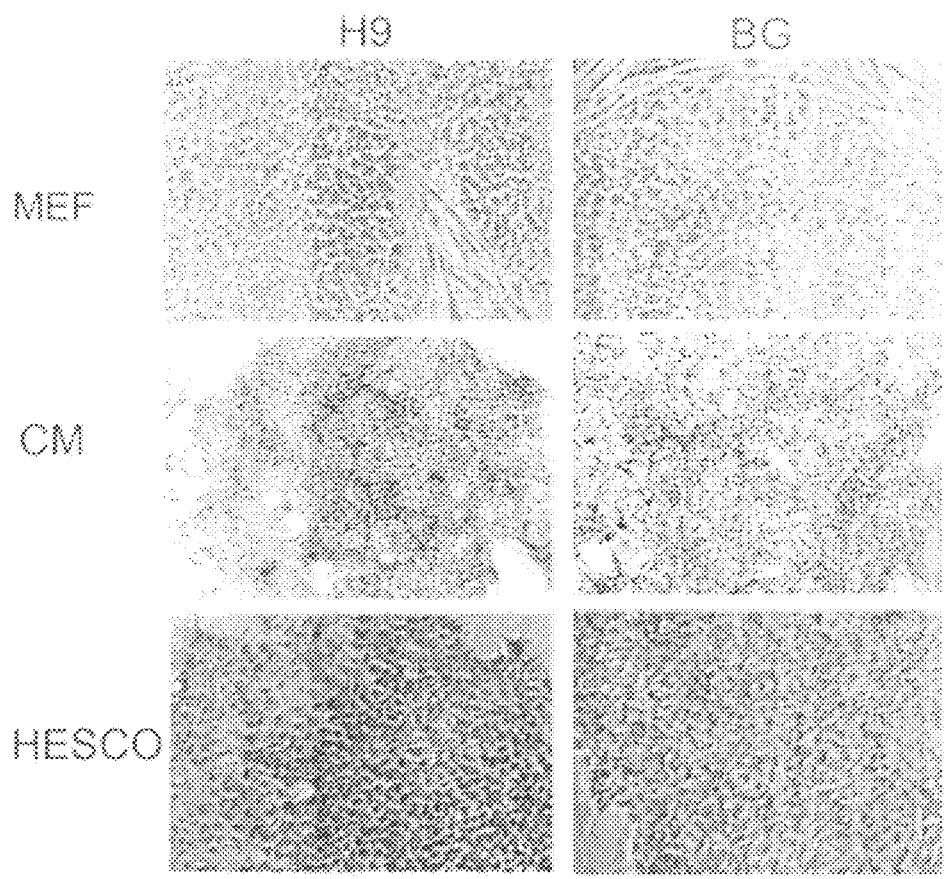
FIGS. 2A and 2B, is a series of images depicting expression of stem cell markers in cultured hESCs.

The present invention features compositions and methods for stem cell culture and maintenance. Specifically, the invention provides a culture medium for stem cells, preferably human embryonic stem cells (hESCs). Advantageously, and in a preferred embodiment, the culture medium of the invention can be formulated as a defined culture medium, essentially free of animal serum and used in culture conditions essentially free of feeder cells. Notably, the defined culture medium supports maintenance and proliferation of embryonic stem cells, such as hESCs, in a substantially undifferentiated state. Advantageously, the defined culture medium supports maintenance and proliferation of embryonic stem cells, preferably hESCs, over numerous in vitro passages. Additionally, the embryonic stem cells cultured in the defined culture medium are substantially undifferentiated, retain their pluripotency and maintain their genomic integrity. In a preferred embodiment, for instance for therapeutic applications, the culture medium of the invention comprises no components, such as feeder cells, conditioned medium, serum and matrix material, purified from a non-human animal source.

More preferably, the culture medium comprises components that are recombinantly synthesized or chemically synthesized.

The culture medium of the invention is useful in a plethora of applications. Stem cells may be proliferated in the medium of the invention, and optionally differentiated, for therapeutic applications. Stem cells cultured in the culture medium of the invention may be used to study cell proliferation and differentiation, including identifying molecules that affect one or both processes; used to screen for drug candidates that affect proliferation, differentiation and/or regeneration; genetically modified and used to produce proteins or other molecules. Other uses will be apparent to the skilled artisan in view of this disclosure and the state of the art.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook et al., 2001, Molecular Cloning, A Laboratory Approach, Cold Spring Harbor Laboratory Press, Cold Spring Harbor, N.Y.; and Ausubel et al., 2002, Current Protocols in Molecular Biology, John Wiley & Sons, New York, N.Y.), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" or "treat" a disease, disorder or condition means reducing the severity and/or frequency of one or more symptoms of the disease, disorder or condition, and encompasses restoring and/or regenerating the function of tissues and/or organs.

As used herein, a "therapeutically effective amount" is the amount of a composition sufficient to provide a beneficial effect to the individual to whom the composition is administered. For instance, with regard to the administration of stem cells to an individual, "therapeutically effective amount" is the amount of stem cells which is sufficient to provide a beneficial effect to the individual to which the cells are administered.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least about three sequential nucleotide residues of the polynucleotide. It is understood that a portion of a polynucleotide may include every nucleotide residue of the polynucleotide.

A "recombinant polynucleotide" refers herein to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Polypeptide" refers to a polymer composed of amino acid residues, related naturally-occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

A "recombinant polypeptide" is one which is produced upon expression of a recombinant polynucleotide.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

Conventional notation is used herein to portray polypeptide sequences: the left-hand end of a polypeptide sequence is the amino-terminus; the right-hand end of a polypeptide sequence is the carboxyl-terminus.

A host cell that comprises a recombinant polynucleotide is referred to as a "recombinant host cell." A gene which is expressed in a recombinant host cell wherein the gene comprises a recombinant polynucleotide, produces a recombinant polypeptide.

A "substitute" of a polypeptide as used herein refers to any molecule that can be used in lieu of the polypeptide in the defined culture medium of the invention, and maintain and proliferate primate stem cells in a substantially undifferentiated state, while maintaining the potential to differentiate into derivatives of endoderm, mesoderm and ectoderm tissues and maintaining the karyotype of the stem cells. Substitutes include fusion proteins, polypeptide fragments and naturally-occurring homologs. Also included are variants having at least about 70%, 80%, 85%, 90% and more preferably 95% sequence identity to the polypeptide, provided they retain at least about 1% and more preferably at least about 25% activity of polypeptide. It is understoond that any and all whole or partial integers between the ranges set forth here are included herein. Variants typically have conservative amino acids mutations at residues involved in the structure and the function of the polypeptide. Residues that are not essential to either structure or function typically tolerate a broader array of amino acid mutations.

As applied to a protein, a "fragment" is at least about 20 amino acids in length. A fragment encompasses a protein with at least about 1 to about 5 amino acids, preferably at least about 1 to about 25 amino acids and more preferably at least about 1-50 amino acids truncated truncated from either or both ends.

"Enriching," as the term is used herein, refers to the process by which the concentration, number, or activity of something is increased from a prior state. For example, a population of 100 hESCs is considered to be "enriched" in hESCs if the population previously contained only 50 hESCs. Similarly, a population of 100 hESCs is also considered to be "enriched" in hESCs if the population previously contained 99 hESCs. Likewise, a population of 100 hESCs is also considered to be "enriched" in hESCs even if the population previously contained zero hESCs.

"Substantially homogeneous," as the term is used herein, refers to a population of a substance that is comprised primarily of that substance, and one in which impurities have been minimized. Typically, a compound is substantially homogenous when at least 10%, more preferably at least 20%, more preferably at least 50%, more preferably at least 60%, more preferably at least 75%, more preferably at least 90%, most preferably at least 99% of the total material (by volume, by wet or dry weight, or by mole percent or mole fraction) and any and all whole or partial integers therebetween in a sample is the compound of interest. Homogeneity can be measured by any appropriate method, e.g., in the case of polypeptides, by column chromatography, gel electrophoresis or HPLC analysis. A compound, e.g., a protein, is also substantially purified when it is essentially free of naturally associated components or when it is separated from the native contaminants which accompany it in its natural state.

"Maintenance" of a cell or a population of cells refers herein to the condition in which a living cell or living cell population is neither increasing nor decreasing in total number of cells in a culture.

"Proliferation" of a cell or population of cells, as the term is used herein, refers to the condition in which the number of living cells increases as a function of time with respect to the original number of cells in the culture.

By the term "applicator" as the term is used herein, is meant any device including, but not limited to, a hypodermic syringe, a pipette, a bronchoscope, a nebulizer, and the like, for administering a composition to a mammal.

As used herein, an "instructional material" includes a publication, a recording, a diagram, or any other medium of expression which can be used to communicate the usefulness of a method and/or composition of the invention in a kit for maintaining, proliferating, or administering any composition recited herein. The instructional material of the kit of the invention may, for example, be affixed to a container which contains a composition of the invention or may be shipped together with a container which contains a composition. Alternatively, the instructional material may be shipped separately from the container with the intention that the instructional material and the composition be used cooperatively by the recipient.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, N.Y.; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

A "defined culture medium" refers herein to a chemically-defined formulation comprised solely of chemically-defined constituents. A defined medium may include solely constituents having known chemical compositions. A defined medium may also include constituents that are derived from known sources. For example, a defined medium may include factors and other compositions secreted from known tissues or cells and is substantially homogenous; however, the defined medium will not include the conditioned medium from a culture of such cells. A defined medium may include specific, known serum components isolated from an animal, including human serum components. Such components are preferably substantially homogeneous. In this context, "known" refers to the knowledge of one of ordinary skill in the art with reference to the chemical composition or constituent "Embryonic stem cells" or "ES cells" are cells obtained from an animal (e.g., a primate, such as a human) embryo, preferably from an embryo that is less than about eight weeks old. Preferred embryonic stages for isolating primordial embryonic stem cells include the morula or blastocyst stage of a pre-implantation stage embryo.

"Embryonic germ cells" or "EG cells" are cells derived from the primordial germ cells of an embryo or fetus that are destined to give rise to sperm or eggs. EG cells are among the embryonic stem cells that can be cultured in accordance with the invention.

"Extracellular matrix" or "matrix" refers to one or more substances that provide substantially the same conditions for supporting cell growth as that provided by an extracellular matrix synthesized by feeder cells. The matrix may be provided on a substrate. Alternatively, the component(s) comprising the matrix may be provided in solution. Matrix substances may be purified from prokaryotic or eukaryotic cells, tissues and/or fluids, or may be chemically synthesized.

A cell culture is "essentially free of feeder cells" when it does not contain exogenously added conditioned medium taken from a culture of feeder cells nor exogenously added feeder cells in the culture, where "no exogenously added feeder cells" means that cells to develop a feeder cell layer have not been purposely introduced for that reason. If the cells to be cultured are derived from a seed culture that contained feeder cells, the incidental co-isolation and subsequent introduction into another culture of some small proportion of those feeder cells along with the desired cells (e.g., undifferentiated primate primordial stem cells) should not be deemed as an intentional introduction of feeder cells. Similarly, feeder cells or feeder-like cells that develop from stem cells seeded into the culture shall not be deemed to have been purposely introduced into the culture.

A cell culture is "essentially free of animal serum" when it does not contain exogenously-added serum, where no "exogenously-added serum" means that serum has not been purposely introduced into the medium. If the cells being cultured produce some or all of the components of serum, or if the cells to be cultured are derived from a seed culture grown in a medium that contained serum, the incidental co-isolation and subsequent introduction into another culture of some small amount of serum (e.g., less than about 1%) should not be deemed as an intentional introduction of serum.

"Substantially undifferentiated" as used herein means that population of stem cells (e.g., primate embryonic stem cells) contains at least about 50%, preferably at least about 60%, 70%, 80%, and even more preferably, at least about 90%, undifferentiated stem cells. Fluorescence-activated cell sorting using labeled antibodies or reporter genes/proteins (e.g., enhanced green fluorescent protein [EGFP]) to one or more markers indicative of a desired undifferentiated state (e.g., a primordial state) can be used to determine how many cells of a given stem cell population are undifferentiated. For purposes of making this assessment, one or more of cell surface markers correlated with an undifferentiated state (e.g., Oct4, SSEA3, SSEA4, Tra-1-60, and Tra-1-81) can be detected. Telomerase reverse transcriptase (TERT) activity and/or alkaline phosphatase can also be assayed. In the context of primate stem cells, positive and/or negative selection can be used to detect, for example, by immuno-staining or employing a reporter gene (e.g., EGFP), the expression (or lack thereof) of certain markers (e.g., Oct4, SSEA3, SSEA4, Tra-1-60, Tra-1-81, SSEA1, nestin, telomerase, Nanog, Sox, alpha feto protein (AFP), GATA, and alkaline phosphatase activity), thereby facilitating assessment of the state of self-renewal or differentiation of the cells.

"Basal medium" as used herein refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of the cells' particular developmental state, the gene(s) encoding the necessary biosynthetic proteins are not being expressed at sufficient levels. A number of basal media are known in the art of mammalian cell culture, such as Dulbecco's Modified Eagle Media (DMEM) and DMEM/F12, although any base medium that can be supplemented with a member of the Wnt family, a tumor necrosis factor (TNF) family member, FGF (or an FGF substitute), insulin (or an insulin substitute), transferrin (or a transferrin substitute), albumin (or an albumin substitute), and cholesterol, and which supports the growth of stem cells, preferably embryonic stem cells, in a substantially undifferentiated state can be employed.

"Isotonic" refers to a solution having essentially the same tonicity (i.e., effective osmotic pressure equivalent) as another solution with which it is compared. In the context of cell culture, an "isotonic" medium is one in which cells can be cultured without an appreciable net flow of water across the cell membranes.

As used herein, "chemically defined cholesterol" refers to a cholesterol composition wherein all of the molecular components of the composition are known. In this context, "known" refers to the knowledge of one of ordinary skill in the art with reference to the chemical composition or constituent. A non-limiting example of chemically defined cholesterol is an Invitrogen product, 250× Cholesterol lipid concentrate (Catalog 12531-018; Invitrogen).

As used herein, a "passage" refers to a round of subculturing. Thus, when cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture may be greater than the passage number. The expansion of cells (i.e., the number of population doublings) during the period between passaging depends on many factors, including but, not limited to, the seeding density, substrate, medium, and time between passaging.

Description of the Invention

The compositions and methods of the invention are useful in the culturing of stem cells, preferably embryonic stem cells, and more preferably primate embryonic stem cells. Preferably primate embryonic stem cells that are cultured using this method are human embryonic stem cells that are true embryonic stem cell lines in that they: (i) are capable of indefinite proliferation in vitro in an undifferentiated state; (ii) are capable of differentiation to derivatives of all three embryonic germ layers (endoderm, mesoderm, and ectoderm), even after prolonged culture; and (iii) maintain a normal karyotype throughout prolonged culture. Embryonic stem cells are, therefore, referred to as being pluripotent.

Stem cells that can be cultured in the medium of the invention may be from any animal, preferably mammals and more preferably, primates. Preferred cell types that can be cultured in a substantially undifferentiated state using the defined culture medium of the invention include stem cells derived from humans, monkeys, and apes. With regard to human stem cells, human embryonic stem cells (hESCs) are preferred. hESCs are derived from an embryo, preferably from a pre-implantation embryo, such as from a blastula or a morula. Stem cells derived from non-primate mammals, such as mice, rats, horses, sheep, pandas, goats and zebras, can also be cultured in the medium of the invention. While the culture medium is preferably used for culturing embryonic stem cells, it may be used for culturing adult stem cells, such as, but not limited to, hematopoietic stem cells (HSCs). The art is replete with information of both embryonic and adult stem cells.

Stem cells, including human embryonic stem cells, cultured in accordance with the invention can be obtained from any suitable source using any appropriate technique, including, but not limited to, immunosurgery. For example, procedures for isolating and growing human embryonic stem cells are described in U.S. Pat. No. 6,090,622. Procedures for obtaining Rhesus monkey and other non-human primate embryonic stem cells are described in U.S. Pat. No. 5,843,78 and international patent publication WO 96/22362. In addition, methods for isolating Rhesus monkey embryonic stem cells are described by Thomson et al., (1995, Proc. Natl. Acad. Sci. USA, 92:7844-7848).

Primate stem cells may also be derived from human embryonic germ (EG) cells. Human EG cells are prepared from primordial germ cells obtained from human fetuses of about 8-11 weeks of gestation. See, for instance, Shamblott et al. (1998, Proc. Natl. Acad. Sci. USA 95:13726-31) and U.S. Pat. No. 6,090,622.

A. Culture Medium

The present invention features a serum-free culture medium for the in vitro maintenance and proliferation of stem cells, preferably embryonic stem cells, wherein the culture is essentially feeder-cell free. This is because it has been shown herein that hESCs can be maintained and proliferated in vitro in a substantially undifferentiated state in the absence of both fibroblast feeder cells, or conditioned medium from fibroblast feeder cells, and animal serum, while maintaining the potential to differentiate into derivatives of endoderm, mesoderm and ectoderm tissues and maintaining the karyotype of the stem cells. Accordingly, the present invention features a defined culture medium useful for the maintenance of stem cells in vitro. However, the novel combination of components described herein may be used to supplement media that are not serum-free or feeder-cell free. In particular, the invention encompasses the exogenous addition of a member of the tumor necrosis factor (TNF) family to any culture medium for stem cells.

A defined culture medium for maintenance of stem cells has a basal medium, fibroblast growth factor (FGF), a member of the Wnt family, insulin, transferrin and a member of the tTNF family and is essentially free of animal serum and feeder cells. Advantageously, this minimal recipe supports maintenance of primate stem cells for at least about 4, preferably at least about 8, more preferably about 10, and still more preferably, at least about 20 passages.

The present invention further features a defined culture medium for the proliferation of embryonic stem cells in vitro. A defined culture medium for the proliferation of embryonic stem cells has a basal medium, FGF, a member of the Wnt family, insulin, transferrin, a member of the TNF family, albumin and cholesterol and is essentially free of animal serum and is used to culture embryonic stem cells essentially free of feeder cells. FGF, a member of the Wnt family, insulin, transferrin, a member of the TNF family, albumin and cholesterol are present in the defined culture medium at a concentration that supports the proliferation of primate stems cells in a substantially undifferentiated state, while maintaining both the pluripotency and the karyotype of the cells. A defined culture medium of the invention for embryonic stem cell, preferably hESC, proliferation supports proliferation of embryonic stem cells in a substantially undifferentiated state, while maintaining the potential to differentiate into derivatives of endoderm, mesoderm and ectoderm tissues and maintaining the karyotype of the stem cells, for at least about 4, preferably at least about 8, more preferably at least about 10, and more preferably still, at least about 26 passages, or for at least one month, more preferably at least about two months, and more preferably still, for at least about 6 months.

TNF family member: Members of the TNF family induce pleiotropic biological responses, including cell growth, differentiation, and even death. TNF family members are synthesized as transmembrane molecules that are frequently cleaved to produce a soluble fragment consisting of the receptor binding domain. The fragments may form trimers. Structural studies have shown that the receptor binding domain, called the TNF homology domain, is shared among TNF family members. Consensus sequences critical for beta sheet formation and trimerization of the TNF homology domain earmark the TNF family.

There are nineteen well-characterized TNF family members in humans. Any TNF family member suitable for culture of stem cells in a substantially undifferentiated state while maintaining the pluripotency in accordance with the invention may be used in the culture medium. Slight sequence variations in these factors are expected to exist between species, and thus the term TNF family member is not species limited. Preferably, the TNF family member used in the culture medium of the invention is BAFF, a BAFF substitute, April, an April substitute or a mixture thereof. The April/BAFF pathway is not a member of one of the seven canonical pathways known to to control most of early developmental processes. Therefore, the use and effectiveness of a member of the TNF family, preferably April and/or BAFF, in a culture medium, and in particular, a defined serum-free culture medium for stem cells, particularly hESCs, is unexpected.

BAFF (B cell activating factor; also called BlyS, TALL-1, THANK, zTNF4 and TNFSF13B) and April (A proliferation-inducing ligand; also called TALL-2, TRDL-1 and TNFSF13) are closely-related TNF family members that play a role in B cell proliferation and survival. Receptors for BAFF include: TACI (TNFRSF13B), BCMA (TNFRSF17) and BAFFR (TNFRSF13C). April also binds to TACI and BCMA.

The soluble, receptor-binding domain of April is comprised by amino acids residues 50 to 250 (SEQ ID NO. 1; nucleotide sequence SEQ ID NO. 2) of the human homolog (Hahne et al., 1998, J. Exp. Med. 188:1185-1190). Amino acids residues 83 to 285 of human BAFF (SEQ ID NO. 3; nucleotide sequence SEQ ID NO. 4) comprises the soluble-receptor binding domain. Structure-function analyses for BAFF and April has been pursued (Karpusas et al., 2002, J. Mol. Biol. 315:1145-1154; Kim et al., 2003 Nat. Struct. Biol. 10:342-8; Liu et al., 2003, Nature 423:49-56; Ni et al., 2004, J. Immunol. 173:7394-400; Wallweber et al., 2004, J. Mol. Biol. 343:283-290; Kayagaki et al., 2002, Immunity 17:515-24; Patel et al., 2004, J. Biol. Chem. 279:16727-35). Furthermore, there are known, functional variants for both April and BAFF. Functional BAFF and April variants are disclosed in U.S. Patent Application No. 20060014248. U.S. Patent Application Nos. 20050003480, 20050130892 and 20050221443 disclose functional April variants and functional BAFF variants. Accordingly, these teachings provide an abundance of structure-function information, enabling the skilled artisan to comprehend with a reasonable expectation of success, what amino acid positions can be mutated in either of April or BAFF and what types of mutations are tolerated.

The TNF family member is preferably from the same primate species as the stem cells intended to be cultured in the culture medium. Thus, for hESCs, preferably, the TNF family member is a human TNF family member.

The preferred range of a member of the TNF family in a defined culture medium of the invention is about 1 ng/ml to about 10,000 ng/ml, preferably about 10 ng/ml to about 1000 ng/ml and more preferably, about 100 ng/ml to about 250 ng/ml. In one embodiment, a TNF family member is present at about 100 ng/ml in the culture medium. It is understood that any and all whole or partial integers between the ranges set forth here are included herein.

Wnt family member: The Wnts (wingless-type MMTV integration site family) are a family of secreted glycoproteins that have been shown to be involved in a variety of developmental processes in many organisms. While any Wnt family member is useful in the culture medium of the invention, the Wnt family member is preferably Wnt3a or a Wnt3a substitute. The amino acid and nucleotide sequences for human Wnt3a are provided as SEQ ID NOs. 5 and 6, respectively. Slight sequence variations in these factors are expected to exist between species, and thus the term Wnt family member is not species limited. Wnt3a is highly homologous to Wnt3 in humans, sharing the Wnt core domain with the 24 conserved cysteines and two N-linked glycosylation sites (Katoh, 2002, Internatl. J. Mol. Med. 9:579-584). The Wnt is preferably from the same species as the stem cells intended to be cultured in the culture medium. Thus, for hESCs, preferably, the Wnt family member is a human Wnt family member and more preferably, it is human Wnt3a.

The invention further envisions the substitution of a member of the Wnt family, preferably Wnt3a, with at least one of: a GSK3 inhibitor, such as 6-bromoindirubin-3'-oxime (Sato et al., 2004, Nat Med. 10:55-63), TGF-beta, noggin (Wang, 2005, Biochem Biophys Res Commun. 330:934-42), nodal (Vallier, 2005, J Cell Sci 118(Pt 19):4495-509), activin A (Beattie, 2005, Stem Cells 23:489-95; Vallier, 2005, J Cell Sci 118(Pt 19):4495-509) and plasmanate (Klimanskaya, 2005, Lancet 365:1636-41).

The preferred range of a Wnt family member in a defined culture medium of the invention is about 0 ng/ml to about 10,000 ng/ml, preferably about 1 ng/ml to about 2000 ng/ml and more preferably, about 100 ng/ml to about 250 ng/ml. In one embodiment, a Wnt family member is present at about 100 ng/ml in the culture medium. It is understood that any and all whole or partial integers between the ranges set forth here are included herein.

Fibroblast growth factor (FGF): FGF as used herein means any FGF suitable for culture of primate stem cells in a substantially undifferentiated state, and includes FGF substitutes. Fibroblast growth factors (FGFs) are essential molecules for mammalian development. There are currently twenty-two known FGFs in vertebrates and four signaling fibroblast growth factor receptors therefor (and their spliced variants). See, for instance, Ornitz et al., (2001, Genome Biol. 2:3005.1-3005.12). A substantial amount of information regarding the structure and function of FGF is available in the art (Ornitz et al., 2001). Furthermore, peptides from bFGF with bFGF receptor agonist activity are known in the art (Baird et al., 1988, Proc. Natl. Acad. Sci. USA 85:2324; Presta et al., 1991, J. Cell Physiol. 149:512-524; Ueno et al., 1986, Regul. Pept. 16:135-145). Slight sequence variations in these factors are expected to exist between species, and thus the term fibroblast growth factor is not species limited. Preferably, the FGF is basic FGF (bFGF; also called FGF-2) or a bFGF substitute. The FGF is preferably from the same species as the stem cells intended to be cultured in the culture medium. Thus, for hESCs, the FGF is preferably a human FGF and more preferably, is human bFGF.

The preferred range of FGF in a culture medium of the invention is about 4 ng/ml to about 10,000 ng/ml, preferably about 4 ng/ml to about 2000 ng/ml, and more preferably about 4 ng/ml to about 100 ng/ml. In one embodiment, FGF is present at about 16 ng/ml in the culture medium. It is understood that any and all whole or partial integers between the ranges set forth here are included herein.

While FGF is preferably used, other materials, such as certain synthetic small peptides (e.g. produced by recombinant DNA variants or mutants) designed to activate fibroblast growth factor receptors, may be used instead of FGF. See, for instance, Yamaguchi et al., 1992, Dev. Biol. 152:75-88.

Insulin: Insulin is a well-characterized polypeptide hormone, which plays an important role in stimulating proliferation of cells and in aiding carbohydrate metabolism. Insulin promotes the uptake of glucose and amino acids by cells. Any insulin suitable for culture of stem cells in a substantially undifferentiated state may be used in the culture medium. Slight sequence variations in insulin is expected to exist between species, and thus the term insulin is not species limited.

The insulin is preferably from the same species as the stem cells intended to be cultured in the culture medium. Thus, for hESCs, preferably, the insulin is human. The insulin component is optional when culturing murine embryonic stem cells.

The preferred range of insulin in a culture medium of the invention is about 10 µg/ml to about 10,000 µg/ml, preferably about 20 µg/ml to about 1000 µg/ml, more preferably about 20 µg/ml to about 200 µg/ml. In one embodiment, insulin is present at about 160 µg/ml in the defined culture medium. It is understood that any and all whole or partial integers between the ranges set forth here are included herein.

Transferrin: The transferrin superfamily is a family of glycoproteins containing an N-terminal and C-terminal iron-binding domains. All members of the transferrin superfamily have similar polypeptide structure. In vivo, transferrins are involved in iron delivery to cells, controlling free iron concentration in biological fluids and preventing iron-mediated free radical toxicity. Slight sequence variations in transferrin is expected to exist between species, and thus the term transferrin is not species limited. The transferrin is preferably from the same species as the stem cells intended to be cultured in the culture medium. Thus, for hESCs, it is preferred that the transferrin is human.

The preferred range of transferrin in a culture medium of the invention is about 5 µg/ml to about 10,000 µg/ml, preferably about 11 µg/ml to about 1000 µg/ml, and more preferably, about 50 µg/ml to about 150 µg/ml. In one embodiment, transferrin is present at about 88 µg/ml in the defined culture medium. It is understood that any and all whole or partial integers between the ranges set forth here are included herein.

The invention further envisions that an iron salt or chelate (e.g., ferric citrate chelate or ferrous sulfate) may be used in the present medium as a substitute for transferrin.

Albumin: Albumin is the major protein in serum. It functions as a carrier protein and a regulator of steroid, thyroid and other lipophilic hormones. It also acts as an antioxidant scavenger. Slight sequence variations in albumin is expected to exist between species, and thus the term albumin is not species limited. The albumin is preferably from the same species as the stem cells intended to be cultured in the culture medium. Thus, for hESCs, preferably, the albumin is human albumin.

The preferred range of albumin in a culture medium of the invention is about 1 mg/ml to about 20 mg/ml, more preferably about 1 mg/ml to about 10 mg/ml. In one embodiment, albumin is present at about 2.5 mg/ml in the defined culture medium. It is understood that any and all whole or partial integers between the ranges set forth here are included herein.

Albumin can be provided by a composition comprising albumin. Non-limiting examples include "serum substitute supplement" (Irvine Scientific, Santa Ana, Calif.), which is a defined composition comprising albumin. AlbuMax™ (Invitrogen) is an isolated bovine albumin product that also contains cholesterol. Use of this product may reduce the amount of exogenous cholesterol needed in the medium. Optimizing cholesterol concentration when using AlbuMax™, or similar products, is not undue experimentation for the skilled artisan.

Cholesterol: In mammalian cells, cholesterol is essential for diverse cellular functions. Structurally, it is involved in lipid raft assembly, modulating membrane rigidity and facilitating post-Golgi sorting. Cholesterol is also the precursor of steroid hormones.

Preferably, the cholesterol is a chemically-defined cholesterol, such as, but not limited to, the "cholesterol lipid concentrate" commercially available from Invitrogen. The 250× Cholesterol lipid concentrate (Catalog 12531-018; Invitrogen) was developed using wild-type NS0 cells grown in suspension with CD Hybridoma Medium (Gorfien et al., 2000, Biotechnol. Prog. 16:682-687). Another commercially available cholesterol product is SyntheChol™ (Sigma-Aldrich), which is a synthetic cholesterol product.

The preferred range of 250× Cholesterol lipid concentrate in a culture medium of the invention is about 1× to about 10×, more preferably about 1× to about 5×. In one embodiment, cholesterol is present at about 2.5× in the culture medium. It is understood that any and all whole or partial integers between the ranges set forth here are included herein.

Alternatively, cholesterol is provided as a solubilized complex of purified or synthetic cholesterol. Cholesterol is not soluble in aqueous media. It is well known in the art to solubilize cholesterol by complexing it with a carrier. A well-known carrier for this purpose is cyclodextrin. See, for instance, U.S. Pat. No. 4,533,637. Three cyclodextrins are employable in such lipid-carrier complexes: alpha-, beta, and gamma-cyclodextrin. While any of the cyclodextrins can be used, beta-cyclodextrin appears to be the best (U.S. Pat. No. 6,372,210). The preparation of such complexes is described, for example, in U.S. Pat. No. 4,533,637 the entire entire contents of which is hereby incorporated by reference. Such complexes are also commercially available, for instance, from Sigma, which offers a "soluble cholesterol" product comprising chlosterol and methyl-beta-cyclodextrin.

Solubilized cholesterol is provided at about 0.00001 µg/ml to 10,000 µg/ml, preferably 0.0001 to 1000 µg/ml and more preferably 0.001 to 100 µg/ml in the defined medium of the invention. It is envisioned that alternatives to cholesterol, methyl cholesterols, various hydroxy-cholesterols, epi-cholesterol, cholesterol, and beta-estradiol, may be used in the culture medium. It is understood that any and all whole or partial integers between the ranges set forth here are included herein.

Substitutes of any of the above described components may be used in the medium of the invention. With regard to polypeptide fragments or variants, structure-function information is available in the art for all of these polypeptide components. Such information provides sufficient guidance to the skilled artisan to prepare suitable fragments or variants of a given component that can be used in lieu of the component in the defined culture medium of the invention, and maintain and proliferate primate stem cells in a substantially undifferentiated state, while maintaining both the potential to differentiate into derivatives of endoderm, mesoderm and ectoderm tissues and the karyotype of the stem cells. Variants can have at least about 70%, 80%, 85%, 90% and more preferably 95% sequence identity to a polypeptide component, provided they retain at least about 25% activity of the polypeptide component. It is understoond that any and all whole or partial integers between the ranges set forth here are included herein.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "http://www(dot)ncbi(dot)nlm(dot)nih(dot)gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www(dot)ncbi(dot)nlm(dot)nih(dot)gov.

The percent identity between two sequences can be determined using techniques similar to those described above, with or without allowing gaps. In calculating percent identity, typically exact matches are counted.

Sequence variants can be created by any means known in the art including, but not limited to, site-specific mutatagenesis, random mutagenesis, PCR mutagenesis, and frame-shift mutations. Further, any other number of procedures may be used for the generation of derivative or variant forms of a sequence variant, using recombinant DNA methodology well known in the art such as, for example, that described in Sambrook et al. (2001, Molecular Cloning: A Laboratory Manual, Cold Spring Harbor Laboratory Press, New York) and Ausubel et al. (2002, Current Protocols in Molecular Biology, Green & Wiley, New York). Nucleotide and amino acid sequences for exemplary components (human April, human BAFF and human Wnt3a) are provided elsewhere herein.

The skilled artisan is familiar with methods to assess whether a molecule can substitute for a component of the defined culture medium of the invention. As a non-limiting example, the proliferation, differentiation and pluripotency of hESCs cultured in a defined medium of the invention is compared to the proliferation, differentiation and pluripotency of hESCs cultured in an identical medium formulation except that a component is substituted by a candidate substitute molecule. The candidate substitute molecule can be tested at a variety of concentrations. A candidate that can support the proliferation, differentiation and pluripotency of hESCs in lieu of a component of the defined medium may substitute for that component.

With regard in particular to a member of the Wnt family and a member of the TNF family, the invention envisions the use of any other molecule, including substitutes of Wnt3a, April and BAFF, which exhibits activity analogous to that observed for Wnt3a, April and BAFF respectively when used in the defined media of the invention. Here, "analogous" does not require an equivalent level of activity per molecule of, for instance, Wnt3a, and another molecular species having the particular activity of Wnt3a in the defined media of the invention. Thus, different amounts of the molecular species substituted for Wnt3a, April and/or BAFF may be required to obtain the same biological effect as achieved using Wnts3a, April and BAFF, as the case may be. Accordingly, a molecule that can be substituted for Wnt3a, April or BAFF, as the case may be, are "functional equivalents" of the molecules for which they are substituted, even if different amounts of the functionally equivalent molecules are required to achieve the same results as can be obtained using a naturally-occurring form of Wnt3a, April or BAFF.

In addition, the invention envisions that the amount of Wnt3a used in a culture medium can be reduced in a medium when the amount of bFGF is increased, and the culture medium will support embryonic stem cell growth in substantially undifferentiated state, while maintaining both the pluripotency of the cells and the karyotype of the cells.

The polypeptide components of the culture medium may contain modifications. Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also included a lipid modifications, such as palmitoylated cysteines. Also embraced are sequences which have phosphorylated amino acid residues, e.g., phosphotyrosine, phosphoserine, or phosphothreonine.

The components used in the defined culture medium of the invention are exogenous additions to basal medium. Thus, although hESCs may themselves express one of the components in the defined culture medium, the teachings herein refer to exogenous components. The components may be obtained from any source. Preferably, however, the components are obtained from non-human animal sources. In one embodiment for culturing hESCs, the components are preferably obtained from a human source. More preferably, and of particular value for therapeutic applications, the components are obtained by chemical synthesis and/or recombinant synthesis. Recombinant synthesis refers to the expression of a recombinant polynucleotide to produce a recombinant polypeptide. Recombinant expression encompasses in vitro translation systems as well as in vivo or ex vivo expression of a recombinant polynucleotide in a host cell. Genes for each of the polypeptide components have been cloned in numerous organisms. Exemplary coding sequences for human homologs include: bFGF (GenBank Accession number NM_002006), Wnt3a (GenBank Accession number NM_033131), BAFF (GenBank Accession number NM_006573), April (GenBank Accession number AF046888), insulin (GenBank Accession number NM_000207), albumin (GenBank Accession number NM_000477) and transferrin (GenBank Accession number NM_001063).

Vectors for expression cassettes and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.J.) and Ausubel et al. (eds., 2002, Current Protocols in Molecular Biology, John Wiley & Sons, New York). Techniques for introducing vectors into target cells include, but are not limited to, electroporation, photoporation, calcium precipitation, fusion, transfection, lipofection, viral targeting and the like.

Any expression vector compatible with the expression of a polypeptide component of the defined culture medium in a host cell is suitable for use in the instant invention, and can be selected from the group consisting of a plasmid DNA, a viral vector, and a mammalian vector. Vectors may be episomal, or may be provided for integration into the target cell genome via homologous recombination or random integration. Viral vectors useful in the methods of the invention include, but are not limited to, cytomegalovirus vectors, adenovirus vectors and retrovirus vectors, such as MigRI, MMLC, HIV-2 and ALV.

The vector comprising the expression cassette, or a vector that is co-introduced with the expression vector, can comprise a marker gene. Marker genes are useful, for instance, to monitor transfection efficiencies. Marker genes include genes for selectable markers, including, but not limited to, G418, hygromycin, and methotrexate, and genes for detectable markers, including, but not limited to luciferase and GFP.

The nucleic acid encoding a polypeptide contained in an expression cassette may, optionally, be fused in-frame to other coding sequences. For instance, the coding sequence of an epitope or other detectable tag may be included. Such tags are useful, for instance, to assist in the rapid purification of the encoded catalytically-inactive dsPTP polypeptide or variant thereof. Non-limiting examples of such tags include a 6-His sequence and a FLAG epitope. The fusion may be at either the N-terminal or the C-terminal of a polypeptide, provided the activity of the polypeptide is maintained.

In the context of an expression vector, the vector may be readily introduced into a host cell, e.g., mammalian, bacterial, yeast or insect cell by any method in the art. For example, the expression vector can be transferred into a host cell by physical, chemical or biological means. Eukaryotic cells are preferred as host cells, for instance, to provide appropriate post-translational modifications.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., supra, 2001 and Ausubel et al., supra, 2002.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, e.g., U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems are well known in the art.

Polypeptides used in the culture medium of the invention are preferably substantially homogenous. Accordingly, using methods well known in the art, a polypeptide is isolated from a biological source, a chemical synthesis or a recombinant synthesis. Non-limiting examples of such methods include bulk fractionation, electrophoretic techniques, and chromatographic techniques. These techniques include: precipitation by salts, pH, and ionic polymers; ion exchange, gel filtration, hydrophobic interaction, and reverse phase chromatography; lectin affinity, ligand affinity, oligonucleotide affinity, and immunoaffinity chromatography; polyacrylamide gel electrophoresis, and electroblotting; and high performance liquid chromatography. Procedures for solubilizing proteins from inclusion bodies and refolding them into active monomeric forms are also known. The isolated polypeptide may be characterized by methods including, but not limited to, immunological and biochemical assays, peptide mapping, amino acid analysis, protein sequencing, and mass spectrometry. See also Marshak et al. (1996, Strategies for Protein Purification and Characterization—A Laboratory Course Manual, CSHL Press); Ausubel et al. (eds., 2002, Current Protocols in Molecular Biology, John Wiley & Sons, New York); Cutler (ed., 2004, Protein Purification Protocols, $2^{nd}$ edition, Humana Press, Totawa, N.J.); Rosenberg (2005, Protein Analysis and Purification: Benchtop Techniques, Birkhäuser, Boston, Mass.); and Roe (ed., 2001, Protein Purification Techniques: A Practical Approach, $2^{nd}$ edition, Oxford University Press, Oxford, UK).

Basal media useful in mammalian cell culture are known in the art. Non-limiting examples of basal media useful in the defined culture medium of the invention include Minimum Essential Medium Eagle, ADC-1, LPM (Bovine Serum Albumin-free), F10 (HAM), F12 (HAM), Dulbecco's Modified Eagle Medium (DMEM—without serum), DMEM/F12, DCCM1, DCCM2, RPMI 1640, BGJ Medium (with and without Fitton-Jackson Modification), Basal Medium Eagle (BME—with the addition of Earle's salt base), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred basal medium for use in the present invention is DMEM/F12. These and other useful media are available from GIBCO, Grand Island, N.Y., USA, and Biological Industries, Bet HaEmek, Israel, among others. A number of these media are summarized in Methods in Enzymology, Volume LVIII, "Cell Culture", pp. 62-72, edited by William B. Jakoby and Ira H. Pastan, published by Academic Press, Inc In some embodiments, the culture medium of the invention may further include any components known by the skilled artisan to be useful in the culturing of primate stem cells, excluding feeder cells, conditioned medium and animal serum. In particular, for embryonic stem cell culture, the medium further comprises glutamine, non-essential amino acids and 2-mercaptoethanol. In an embodiment, a serum-free defined medium may include at least one additional growth factor. Growth factors useful in the present invention include, but are not limited to, stem cell factor (SCF), glial cell line-derived neurotrophic factor (GDNF), GDNF-family receptor (including GFRα1), leukemia inhibitory factor (LIF), hepatocyte growth factor (HGF), acidic fibroblast growth factor (aFGF), epidermal growth factor (EGF), insulin-like growth factor (including IGF-1 and IGF-2), keratinocyte growth factor (KGF), nerve growth factor (NGF), transforming growth factor beta (TGF-.beta.), vascular endothelial cell growth factor (VEGF), platelet-derived growth factor (PDGF), transforming growth factor (including TGF-β I through V, as well as the TGF-β superfamily: BMP-1 through 12, GDF-1 through 8, dpp, 60A, BIP, OF), various interleukins (such as IL-1 through IL-18), various colony-stimulating factors (such as granulocyte/macrophage colony-stimulating factor (GM-CSF)), Sonic hedgehog, notch, leptin, hormones, and various interferons (such as IFN-gamma). It is further recognized that additional components may be added to the culture medium, provided they support substantially undifferentiated proliferation of primate stem cells, particularly hESCs, and maintain both pluripotency and karyotype of the cells. Such components may be biologically-relevant lipids, antibiotics, antimycotics, anti-oxidants (reducing agents), amino acids, and other components known to the art for the culture of cells, excluding feeder cells, conditioned medium and animal serum. Biologically-relevant lipids include neutral triglycerides of predominantly unsaturated fatty acids such as linoleic, oleic, palmitic, linolenic, and stearic acid, as well as phospholipids such as phosphatidylethanolamine and phosphatidylcholine. Anti-oxidants useful in the defined medium of the invention include, but are not limited to, β-mercaptoethanol, ascorbic acid, monothioglyceroll and dithiothreitol. Antibiotics that can be added into the medium include, but are not limited to, penicillin and streptomycin. Additionally, components may be added to or removed from the medium to induce or enhance the differentiation process.

Preferably, the components are free of endotoxins. Endotoxins are a pyrogen, which is defined as a substance that can cause a fever response. Endotoxins are also toxic to cells grown in tissue culture conditions.

In preferred embodiments, a medium's endotoxicity, as measured in endotoxin units per milliliter ("eu/ml"), will be less than about 0.1 eu/ml, and, in more preferred embodiments, will be less than about 0.05 eu/ml. In particularly preferred embodiments, the endotoxicity of the base medium will be less than about 0.03 eu/ml. Methods for measuring endotoxicity are known in the art. For example, a preferred method is described in the "Guideline on Validation of the Limulus Amebocyte Lysate Test as an End-product Endotoxin Test for Human and Animal Parental Drugs, Biological Products and Medical Devices," published by the U.S. Department of Health and Human Services, FDA, December 1987.

The defined culture medium of the invention may be used as part of a culture system to culture primate stem cells. A culture system of the invention comprises a defined culture medium of the invention and a matrix. Matrices useful in a culture system of the invention include, but are not limited to, fibronectin, collagen, laminin, vibronectin, heparan sulfate, poly-D-lysine, peptides, matrigel and combinations thereof. Examples of fibronectin useful in the invention include, but are not limited to, plasma fibronectin, cellular fibronectin, and synthetic fibronectin. Preferably, collagen is collagen IV. Preferably, the matrix is fibronectin, collagen or a combination thereof. Preferably, the matrix is obtained by recombinant or chemical synthesis, or is obtained from a human biological sample.

Typically, the matrix is applied to the surface of a culturing vessel, such as a culture plate or flask. The culturing vessel further contains the defined culture medium of the invention. Alternatively, the matrix is provided in a soluble form in the defined culture medium.

For use in a culture system of the invention, fibronectin is applied to a surface at between about 5 µg/cm² to about 250 µg/cm². Collagen is applied at between about 20 µg/cm² to about 50 µg/cm². When fibronectin and collagen are used together, the same concentration ranges are suitable. Laminin is applied at between about 20 µg/cm² to about 50 µg/cm². Matrigel is applied at between about 50 µg/cm². Concentrations for use in soluble form can be readily assessed from the art. In addition, the skilled artisan is readily able to optimize matrix concentrations for soluble use without undue experimentation B. Compositions for Preparing Culture Medium The invention further provides a composition useful for preparing a culture medium, preferably a defined, serum-free culture medium, of the invention. In one embodiment, the composition of the invention is useful as a supplement to a basal medium for preparing a defined culture medium that is essentially free of animal serum and which is useful for maintaining stem cells, preferably embryonic stem cells, in culture essentially free of feeder cells. Necessary culture medium components not present in the composition are provided separately to the basal medium. In another embodiment, the composition is an all-but-complete medium. Components not present in the all-but-complete medium are provided separately to the all-but-complete medium to make the defined culture medium of the invention. In another embodiment, the composition is used as a supplement to a medium that comprises animal serum, feeder cells or conditioned medium.

In one embodiment, the composition comprises a member of the Wnt family and a member of the TNF family. This composition is added, for instance, to a culture medium comprising a basal medium, FGF, insulin, and transferrin to maintain stem cells in culture. For a culture medium useful for proliferating stem cells, the composition is added to culture medium comprising a basal medium, FGF, insulin, transferrin, albumin and cholesterol.

In another embodiment, the composition comprises a member of the TNF family and one of insulin, albumin or transferrin. The composition is added to a medium comprising the other components of the culture medium of the invention in order to prepare the culture medium. This composition is advantageous in allowing the skilled artisan to prepare a culture medium of the invention comprising a Wnt family member and FGF, or to prepare a culture medium comprising an elevated amount of FGF and an appropriately-reduced amount of a Wnt family member to prepare a culture medium of the invention.

The composition may further comprise one or more additional components of the culture medium of the invention. Such a composition is added to an appropriate incomplete culture medium in order to make the culture medium of the invention.

In one embodiment, therefore, the composition comprising a member of the Wnt family and a member of the TNF family further comprises at least one of insulin and transferrin. In one aspect, the composition further comprises both insulin and transferrin. In another embodiment, the composition further comprises albumin, insulin and transferrin. In yet another embodiment, the composition further comprises albumin, insulin, transferrin and cholesterol. In yet another embodiment, the composition further comprises albumin, insulin, transferrin, cholesterol and FGF. The composition of this embodiment is useful for preparing a defined culture medium that is essentially free of animal serum and which is useful for proliferating embryonic stem cells in culture that is essentially free of feeder cells.

Similarly, in another embodiment, the composition comprising a member of the TNF family and, for instance, insulin, further comprises albumin. In another embodiment, the composition further comprises transferrin. In yet another embodiment, the composition further comprises both albumin and transferrin. In yet another embodiment, the composition comprises cholesterol.

Further provided by the invention is a composition that is an all-but-complete formulation of a culture medium of the invention comprising a basal medium, a member of the Wnt family, a member of the TNF family, insulin, transferrin, albumin and cholesterol. This all-but-complete medium is supplemented with FGF and, optionally, 2-mercaptoethanol, to prepare a culture medium of the invention suitable for proliferating stem cells. The all-but-complete medium may be further supplemented with glutamine and non-essential amino acids for preparing a defined culture medium for proliferating embryonic stem cells.

The compositions of the invention may be packaged as a liquid or as a solid. A liquid composition may be frozen or non-frozen. Alternatively, the composition according to the present invention can be in the form of an emulsion, colloidal suspension, or a combination thereof. For example, an aqueous solution of a water-soluble composition can be combined with an aqueous suspension of a water-insoluble component, for instance, cholesterol, to form a composition according to the present invention.

In any formulation, the composition may contain additional ingredients intended to preserve and stabilize the components of the composition, where such additional ingredients do not compromise the capacity of the defined culture medium to maintain and proliferate embryonic stem cells, particularly hESCs, in a substantially undifferentiated state while maintaining pluripotency of the cultured cells. Such ingredients include buffering systems and any excipients intended to stabilize the biopharmaceutical substance in the liquid or solid form, such as a lyoprotectant. See for instance U.S. Pat. No. 7,060,268.

A solid formulation typically comprises lyophilized (freeze-dried) polypeptides. Lyophilization is a commonly employed technique for preserving proteins which serves to remove water from the protein preparation of interest. It is a process by which the material to be dried is first frozen and then the ice or frozen solvent is removed by sublimation in a vacuum environment. An excipient (a lyoprotectant) may be included in pre-lyophilized formulations to enhance stability during the freeze-drying process and/or to improve stability of the lyophilized product upon storage (Pikal, 1990, M. Biopharm. 3(9)26-30; and Arakawa et al., 1991, Pharm. Res. 8(3):285-291). A "lyoprotectant" is a molecule which, when combined with a protein of interest, significantly prevents or reduces chemical and/or physical instability of the protein upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. The preferred lyoprotectant is a non-reducing sugar, such as trehalose or sucrose.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage A "bulking agent" is a compound which adds mass to the lyophilized mixture and contributes to the physical structure of the lyophilized cake (e.g. facilitates the production of an essentially uniform lyophilized cake which maintains an open pore structure). Exemplary bulking agents include mannitol, glycine, polyethylene glycol and xorbitol.

Preferably, the compositions comprising ingredients of the culture medium of the invention are more concentrated than the concentration of the same ingredients in a 1× medium formulation. The ingredients can be 10-fold more concentrated (10× formulation), 20-fold more concentrated (20× formulation), 25-fold more concentrated (25× formulation), 50-fold more concentrated (50× concentration), or 100-fold more concentrated (100×. formulation). More highly concentrated formulations can be made, provided that the ingredients remain soluble and stable. See U.S. Pat. No. 5,474,931, which disclose methods of solubilizing culture media components at high concentrations.

If the medium ingredients are prepared as separate, concentrated solutions, an appropriate (sufficient) amount of each concentrate is combined with a basal medium to produce a 1× medium formulation. If the medium ingredients are prepared as solids, an appropriate (sufficient) amount of an appropriate diluent is combined to reconstitute the solids as a suspension or solution. The diluent may be water, but other solutions including a basal medium, aqueous buffers, aqueous saline solution, or other aqueous solutions may be used according to the invention.

The culture media and compositions of the present invention are typically sterilized to prevent unwanted contamination. Sterilization may be accomplished, for example, by filtration through a low protein-binding membrane filter of about 0.1-1.0 μm pore size (available commercially, for example from Millipore) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1× sterile medium formulation. Autoclaving or other elevated temperature-based methods of sterilization are not favored, since many of the components of the present culture media are heat labile and will be irreversibly degraded by temperatures, such as those achieved during most heat sterilization methods.

The compositions, including the media, of the invention may be packaged in numerous ways, as the skilled artisan will recognize. Any container that can contain a sterile composition and maintain the sterility and functional integrity of the composition is suitable for the composition. Non-limiting examples of containers are vials, ampules, tubes, flasks, bottles, such as flexible bottles, and flexible bags.

C. Methods using the Culture Medium

Stem cells are cultured in the medium of the invention according to methods well known in the art. See, for example, Sambrook et al. (2001, Molecular Cloning: A Laboratory Manual, Cold Spring Harbor Laboratory Press, Cold Spring Harbor, N.Y.); Ausubel et al. (eds., 2002, Current Protocols in Molecular Biology, John Wiley & Sons, New York); Gerhardt et al. (eds., 1994, Methods for General and Molecular Bacteriology, American Society for Microbiology, Washington, D.C.); Cellis et al. (eds, 1994, Cell Biology: A Laboratory Handbook, Volumes I-III, Academic Press, San Diego, Calif.; Freshney (2000, Culture of Animal Cells—A Manual of Basic Technique, 4th edition, Wiley-Liss, New York, N.Y.); Freshney ed, (1992, Animal Cell Culture, A Practical Approach, IRL Press, Oxford, UK); Robertson (ed, 1987, Teratocarcinomas and Embryonic Stem Cells: A Practical Approach, IRL Press, Oxford, UK); Pollard et al. (1990, Animal Cell Culture. Methods in Molecular Biology, Vol. 5, Humana Press, Totawa, N.Y.); and Thomson et al. (1998, Primate embryonic stem cells. Current Topics in Developmental Biology 38: 133-165); Marshall et al. (2001, Isolation and maintenance of primate embryonic stem cells. Methods in Molecular Biology 158:11-18); all of which are incorporated herein in their entirety.

Any suitable culture vessel can be adapted to culture stem cells (e.g., primate embryonic stem cells) in accordance with the invention. For example, vessels having a substrate suitable for matrix attachment include tissue culture plates (including multi-well plates), pre-coated (e.g., gelatin-pre-coated) plates, T-flasks, roller bottles, gas permeable containers, and bioreactors. To increase efficiency and cell density, vessels (e.g., stirred tanks) that employ suspended particles (e.g., plastic beads or other microcarriers) that can serve as a substrate for attachment of an extracellular matrix can be employed. In other embodiments, undifferentiated stem cells can be cultured in suspension by providing the matrix components in soluble form. As will be appreciated, fresh medium can be introduced into any of these vessels by batch exchange (replacement of spent medium with fresh medium), fed-batch processes (i.e., fresh medium is added without removal of spent medium), or ongoing exchange in which a proportion of the medium is replaced with fresh medium on a continuous or periodic basis. Large-scale culturing devices and continuous cell culture systems are known in the art. See, for instance, Ulloa-Montoya et al. (2005, J. Biosci. Bioengineer. 100:12-27).

The culture medium of the invention may be used to maintain and proliferate primate stem cells, preferably hESCs, for use in any known application using primate stem cells. Methods of using primate stem cells, particularly hESCs, are well known in the art. See, for instance, U.S. Pat. Nos. 6,800,480, 7,041,438 and U.S. Patent Application No. 20050233446. Several representative examples of such applications are described.

One valuable application is the use of the instant cell culture medium and method of culturing embryonic stem cells in screening assays to identify growth factors useful in culturing embryonic stem cells in an undifferentiated state. Similarly, stem cells, particularly embryonic stem cells, cultured in the culture media of the invention may be used to identify compounds that induce such cells to differentiate toward a particular cell or tissue lineage. Preferably, a defined culture medium formulation of the invention is used in such applications. In some embodiments, one or more components of the defined culture medium is an animal product. In some embodiments, the defined culture medium has no non-human animal products as components.

Stem cells cultured in the defined culture medium may be used to create new stem cells lines, particularly new hESC cell lines. For instance, new hESC cell lines from diverse genetic backgrounds are important for building the bank of hESC cell lines with different HLAs for therapeutic use. The establishment of new cell lines according to the invention includes normal stem cell lines, as well as abnormal stem cell lines, for example, stem cell lines that carry genetic mutations or diseases (e.g., stem cells infected with a pathogen such as a virus, for example, HIV). Stem cells may also be genetically modified for research, assay and therapeutic applications.

Stem cells cultured according to the invention can be genetically modified to, for example, alter (i.e., increase or decrease) the expression of one or more endogenous genes, and/or express one or more genes introduced into the cells. Methods for genetically modifying cells as well known in the art and are disclosed elsewhere herein. See also Lebkowski et al. (2001, Cancer J. 7 Suppl 2:S83-S93), Liu et al. (2004, Stem Cells Dev. 13:636-45) and Gropp et al. (2003, Mol. Ther. 7:281-287) regarding genetically modifying hESCs. Such genetic modifications can serve, for example, to correct genetic defects detected in a particular stem cell line, as well as to generate abnormal cell lines (which may be useful as model systems that mimic or replicate a genetic context correlated with a particular disease state). New cell lines may be created from genetically modified stem cells, particularly hESCs, cultured in a defined culture medium of the invention.

Cells produced using the compositions and methods of the invention can also be used for drug screening, for instance by mounting them on surfaces to form biosensors. The invention also provides for the capacity to produce, for example, commercial grade undifferentiated embryonic stem cells (e.g., hESCs) on a commercial scale. As a result, stem cells such as primate embryonic stem cells produced in accordance with the present invention have numerous therapeutic and diagnostic applications.

Stem cells cultured in accordance with the present invention can be differentiated into different tissue/stem/progenitor cells in vitro, including, but not limited to, pancreatic cells, neuronal cells, hepatic cells, osteoclast cells and other adult stem cells/progenitor. Such differentiated cells can be used therapeutically, for instance, for organ replacement, wound healing, and development correction. Alternatively, differentiated cells may used in drug screening applications, as well as research applications, for instance, to study cell proliferation and differentiation.

hESCs provide a virtually unlimited source of pluripotent cells which can be used to reprogram differentiated cells into stem cells by, for instance, nuclear transfer, cell extract incubation, or other technology. See, for instance, Tada et al. (2001, Curr. Biol. 11:1553-58) and Serov et al. (2001, An. Acad. Bras. Cienc. 73:561-8). Accordingly, hESCs cultured according to the invention can be used to reprogram differentiated cells.

Unlike existing hESCs cultured using conventional techniques, hESCs, such as those from new hESC cell lines created using a defined medium of the invention, and their derivatives, prepared and cultured in defined culture medium of the invention can be used therapeutically since they will not have been exposed to animal feeder cells, feeder-cell conditioned media, or serum at some point of their life time, thereby avoiding the risks of: contaminating human cells with non-human animal cells, transmitting pathogens from non-human animal cells to human cells, forming heterogeneous fusion cells, and exposing human cells to toxic xenogeneic factors. Conditions that may be treated by the transplantation of ES cell-derived cells include, but are not limited to, Parkinson's disease, Alzheimer's disease, multiple sclerosis, amyotrophic lateral sclerosis, cardiac infarcts, stoke, juvenile-onset diabetes mellitus, liver disorders, dysplasia disorders, and neoplastic diseases, such as leukemia. See, for instance, Rossant et al. (1999, Nat. Biotechnol. 17:23-4) and Gearhart (1998, Science 282:1061-2). hESCs cultured according to the invention can also be used to prepare a medicament useful in stem cell transplantation therapies.

In such therapeutic applications, a therapeutically effective amount of cells is administered to a recipient in need thereof. Between about 1 and about $10^{20}$ cells per 100 kg person are administered to a human. In some embodiments, between about $10^3$ and about $10^{12}$ cells are administered per 100 kg person. In other embodiments, between about $10^5$ cells and about $10^{10}$ cells are administered per 100 kg person. The cells can be administered to a person by various methods including, but not limited to, infusion and intravenous administration. Therapeutic methods may include a single administration of cells or multiple administrations over the course of several days to weeks, months and years. Therapeutic administration of tissues or organs generated from stem cells cultured in the culture medium of the invention is also included.

The cells may be administered to a recipient subject in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere. A preferred method of administration is intravenous infusion.

Stem cells, preferably hESCs, cultured accordance with the invention may be isolated by any suitable technique. Such techniques include affinity chromatography, panning, and fluorescence-assisted cell sorting. Such techniques each employ one or more separation reagents (for example, but not restricted to, antibodies and antibody fragments, reporter genes/proteins, etc.) that are specific for a cell-based marker indicative of an undifferentiated state. In the context of substantially undifferentiated human embryonic stem cells, such markers include, for example, but not restricted to, the transcriptional factor Oct4, and cell surface markers SSEA3, SSEA4, Tra-1-60, and Tra-1-81. Other markers include Nanog, GCTM-2, TG-30, TG-343 and any appropriate marker identified in the future. Negative selection can also be employed, whereby cells that express one or more markers indicative of other than a substantially undifferentiated state, or alternatively, cells which fail to express a particular marker, can be removed from the desired cell population.

A stem cell, preferably a embryonic stem cell, may be identified as being "maintained" in the culture medium by assessing the activity of a stem cell at various time points in the culture medium and comparing the activity with the activity of the stem cells at the start of the culture period. As will be understood by the skilled artisan, little or no loss of activity is an indication that stem cells have been maintained in culture.

In another embodiment, the invention features a method of proliferating stem cells, preferably embryonic stem cells, in a culture medium of the invention. The method includes providing at least one stem cell in a culture medium. In one embodiment, at least one stem cell is proliferated in a culture system described elsewhere herein comprising the culture medium of the invention and a matrix. In preferred embodiments for maintaining and proliferating stem cells, the culture medium is a defined culture medium that is essentially free of animal serum and can be used in essentially feeder free culture conditions.

A stem cell may be identified as being "proliferated" in the culture medium by assessing the stem cell activity at various time points in the culturing process and comparing the activity with the activity of the stem cell at the start of the culture period. An increase in the activity between the start of the culture period and any later time point is an indication that stem cells have been proliferated.

Additionally, the degree of proliferation of stem cells in a culture conditions of the present invention may be assessed by counting the number of cells present at a specific point in time during stem cell culture and comparing the value to the number of cells present at the start of the culture period. Based on the disclosure set forth herein, the skilled artisan will understand that these and other methods of assessing stem cell maintenance and proliferation may be used. These methods include, but are not limited to, FACS and MACS.

The present invention includes a method of determining the effect of a compound on an stem cell, preferably an hESC. In one embodiment, the method uses serum- and feeder-cell-free culture conditions, wherein a first population of enriched stem cells is cultured in a culture system comprising a serum-free defined culture medium, and a matrix. The stem cell culture is contacted with at least one compound, and the activity of said first population of enriched stem cells is assessed. The assessed activity of the first population of enriched stem cells is compared with the assessed activity of a second population of enriched stem cells, wherein the second population of said stem cells is cultured in culture conditions without the compound but is otherwise identical to culture conditions used in conjunction with the first population of enriched stem cells.

A higher level of stem cells activity in the population of first enriched stem cells is an indication that the compound enhances the activity of an stem cell. A lower level of stem cell activity in the population of first enriched stem cells is an indication that the compound inhibits the activity of a stem cell.

As will be understood by the skilled artisan, any compound, from any source, can be used in the screening methods of the present invention. This is because a method of the present invention will provide information regarding the effect, or absence thereof, of any compound on an stem cell in a cell culture medium, preferably a defined culture medium, of the invention. Compounds can be tested individually or in combinations. Compounds that may be tested in such a method include drug candidates and growth factors. Growth factors useful in the present invention include, but are not limited to, stem cell factor (SCF), glial cell line-derived neurotrophic factor (GDNF), GDNF-family receptor (including GFRα1), leukemia inhibitory factor (LIF), acidic fibroblast growth factor (aFGF), epidermal growth factor (EGF), insulin-like growth factor (including IGF-I), platelet-derived growth factor (PDGF), transforming growth factor (including TGF-β I through III, as well as the TGF-β superfamily BMP-1 through 12, GDF 1 through 8, dpp, 60A, BIP, and OF), Sonic hedgehog and notch. Drug candidates may be peptides, polypeptides, nucleic acids, extracts from plant, yeast or bacterial cells or from environmental samples, such as soil, and small molecules. The skilled artisan is familiar with libraries of peptides or small molecules useful as lead drug candidates.

D. Kits

The invention includes various kits useful in preparing and using the define culture medium of the invention. Although exemplary kits are described below, the contents of other useful kits will be apparent to the skilled artisan in light of the present disclosure. Each of these kits is included within the invention.

In one aspect, the invention features a kit for preparing a culture medium for stem cells, comprising a composition comprising a protein comprising a member of the Wnt family and a protein comprising a member of the tumor necrosis factor (TNF) family and instructional material, wherein the instructional material comprises instructions for the use of the kit to prepare a culture medium. In one embodiment, the composition further comprises a protein comprising insulin, a protein comprising tranferrin, a protein comprising albumin and/or cholesterol.

In one aspect, the invention features a kit for preparing a culture medium for stem cells, comprising a composition comprising a protein comprising a member of the tumor necrosis factor (TNF) family and one of a protein comprising insulin, a protein comprising transferrin and a protein comprising albumin, and instructional material, wherein the instructional material comprises instructions for the use of the kit to prepare a culture medium. In one embodiment, the composition comprises a protein comprising a member of the tumor necrosis factor (TNF) family, a protein comprising insulin, a protein comprising tranferrin and a protein comprising albumin. The composition may further comprise cholesterol. In one aspect, the cholesterol is provided in a container separate from the composition.

In one aspect, the invention features a kit for maintaining at least one stem cell in a serum-free culture medium, comprising a defined culture medium essentially free of animal serum and instructional material, wherein the instructional material comprises instructions for the use of the kit to culture at least one stem cell in serum-free and feeder-cell free culture conditions. In another aspect, the invention features a kit for proliferating at least one stem cell in a serum-free culture medium, comprising a defined culture medium essentially free of animal serum and instructional material, wherein the instructional material comprises instructions for the use of the kit to proliferate at least one stem cell in serum-free and feeder-cell free culture conditions.

The invention also features a kit for administering a population of enriched primate stem cells to a mammal, comprising a defined culture medium essentially free of animal serum, a matrix, an applicator, and instructional material, wherein the instructional material includes instructions for the use of the kit to proliferate at least one stem cell in serum-free and feeder-cell free culture conditions and for the applicator-based administration of the stem cells to a mammal.

In some embodiments, the culture medium in a kit of the invention comprises a basal medium, a protein comprising a fibroblast growth factor (FGF), a protein comprising a member of the Wnt family, a protein comprising insulin, a protein comprising transferrin and a protein comprising a member of the tumor necrosis factor (TNF) family. More preferably, it comprises a basal medium, a protein comprising fibroblast growth factor (FGF), a protein comprising a member of the Wnt family, a protein comprising insulin, a protein comprising transferrin, a protein comprising a member of the tumor necrosis factor family, a protein comprising albumin and cholesterol. In some embodiments, the protein comprising a member of the TNF family is selected from the group consisting of April, an April substitute, BAFF, a BAFF substitute and combinations thereof. In some embodiments, the protein comprising a Wnt family member is Wnt3a of a Wnt3a substitute. In some embodiments, the instructional material may comprise instructions for the use of the kit to prepare a defined culture medium that is essentially free of animal serum and, optionally, how to use it in essentially feeder-cell-free culture conditions. In some embodiments, the instructional material may comprise instructions for supplementing the culture medium with one or more of glutamine, non-essential amino acids and 2-mercaptoethanol.

In some embodiments, the kit further comprises a matrix. Preferably, the matrix in a kit of the invention is selected from the group consisting of fibronectin, collagen, laminin, heparan sulfate, poly-D-lysine, peptides and a combination thereof. More preferably, the matrix is selected from the group consisting of fibronectin, collagen and a combination thereof.

A kit of the invention may contain any combination of formulations and containers. The instructional material will comprise guidance on how to reconstitute any lyophilized compositions. In some embodiments, the composition in a kit is in a single container. In other embodiments, the components of the composition are in two or more containers. In some embodiments, the composition is a liquid formulation. In some embodiments, the composition is a solid. In some embodiments, the kit further comprises a sterile aqueous diluent provided to suspend the solid. The diluent may be in a separate container or may be in a container connected to the container with the composition such that the diluent may be added to the composition in a controlled, sterile manner. In some embodiments, the polypeptides of the composition are in one container as a liquid or solid, and the cholesterol is in a separate container as a liquid or solid. Neither the formulation nor the type of container holding a composition of the invention should be construed as a limitation on the invention.

The particular applicator included in a kit will depend on, e.g., the method and/or the composition used to introduce a population of enriched primate stem cells to a mammal. Such applicators are well-known in the art and may include, among other things, a membrane, an implant, a syringe, and the like. Moreover, the kit comprises an instructional material for the use of the kit. These instructions simply embody the disclosure provided herein.

The kit may also include a pharmaceutically-acceptable carrier. Further, the route of administration includes, but should not be limited to, direct contact with the desired site of administration, as well as contact with a cell or tissue adjacent to the desired site of administration.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Experimental Example 1

Medium Containing Minimal Components Supports HESC Growth

The materials and methods used in this example and the following examples are now described.

Cell Culture: Two hESC lines, H9 (Wicell Research Institute, Madison, Wis.) and BG01 (BresaGen, Athen, Ga.), were initially cultured in Dulbecco's Modified Eagle's Medium/Nutrient Mixture F-12 Ham's (DMEM/F12) and supplemented with 20% Knockout™ serum replacement, 1 mM L-glutamine, 1% non-essential amino acid, and 4 ng/ml human basic fibroblast growth factor (bFGF) (all from Invitrogen, Carlsbad, Calif.), and 0.1 mM 2-mercaptoethanol (Sigma, St. Louis, Mo.). CF-1 mouse embryonic fibroblasts (MEF) were used as the feeder cells (Chemicon, Temecula, Calif.). Conditioned medium (CM) was prepared using MEF as described previously (Thomson et al., 1998, Curr Top Dev Biol 38: 133-65; Xu et al., 2001, Nat Biotechnol 19: 971-4; Zeng et al., 2004, Stem Cells 22: 292-312).

All hESC experiments were performed between passages 25-60 from their initial establishment. Cells were passaged every 4-6 days with 1 mg/ml collagen IV or 0.0025-0.25% trypsin-EDTA (Invitrogen). After phosphate-buffered saline (PBS) washing, the cells were dispersed by scraping.

The culture plates were coated with Matrigel™ Matrix (0.33 mg/ml; BD Biosciences, Palo Alto, Calif.), fibronectin (25 ug/ml; Invitrogen), collagen (50 ug/ml) or laminin (50 ug/ml). Fibronectin and collagen was present at 25 ug/ml and 50 ug/ml, respectively, in combination. HESCO contains bFGF (16 ng/ml; Invitrogen), insulin (160 ug/ml; Invitrogen or Sigma), transferrin (88 ug/ml; Invitrogen or Sigma), Wnt3a (100 ng/ml; R&D Systems, Minneapolis, Minn.), April or BAFF (100 ng/ml; R&D Systems), albumin (2.5 mg/ml; Sigma), and cholesterol lipid supplement (2.5×; Invitrogen) in DMEM/F12, further supplemented with glutamine, non-essential amino acids and 2-mercaptoethanol. All of the protein components were human, with the exception of Wnt3a, which was recombinant murine Wnt3a.

Immunofluoresence Assay: Cells were fixed with 4% paraformaldehyde for 15 minutes or methanol for 3 minutes at room temperature. After incubation with anti-SSEA3 (Developmental Studies Hybridoma Bank, Iowa, IA), anti-SSEA4 (Developmental Studies Hybridoma Bank), anti-TRA-1-60 (Chemicon), anti-TRA-1-81 (Chemicon), anti-alpha fetoprotein (Sigma), anti-smooth muscle actin (Sigma), anti-beta tubulin III (Sigma), control mouse IgG and IgM (Sigma), or control rat IgM (eBioscience, San Diego, Calif.; Dako, Norden, Produktionsvej, Denmark), the cells were washed with PBS and incubated with 200-fold diluted fluorescein isothiocyanate (FITC)-conjugated anti-mouse immunoglobulin G antiserum (all from Jackson ImmunoResearch Laboratories, West Grove, Pa.). The cells were also counterstained with DAPI (Roche, Basel, Switzerland) and examined under a fluorescence microscope.

Alkaline Phosphatase Assay: The cells were fixed with 4% paraformaldehyde at room temperature for 15 minutes and washed with PBS. The alkaline phosphatase assay was performed using an ES cell characterization kit (Chemicon).

Karyotyping: hESCs grown in log phase were harvested and karyotyped using Giemsa stain (Genzyme Genetics, Santa Fe, N.M.). Twenty cells were scored in each case.

Embryoid Body Formation: One monoplate of hESCs passaged with 0.025% trypsin was cultured in an uncoated 10 cm Petri-dish in the presence of DMEM supplemented with 10% fetal calf serum (Invitrogen). After 4 days of suspension culture, the embryoid bodies were formed and the cells were transferred to a plate coated with 0.2% gelatin (Sigma). The cells attached to the plate and were cultured for more than 10 days. The cells were fixed and processed for immunofluoresence studies.

Teratoma Formation: Ten (10) million hESCs were subcutaneously injected into SCID-Beige mice (Charles River Laboratories, Wilmington, Mass.). All animal experiment procedures followed the Yale IACUC protocols. The teratomas were harvested at least six weeks after hESC injection. Teratomas were processed with formalin, sectioned with an Excelsior Processor (Thermo Electron Corporation, Pittsburgh, Pa.), and embedded in paraffin (Blue Ribbon, Surgipath Medical Industries, Inc., Richmond, Ill.). Tissue sections were cut at 5 to 6 microns and stained with hematoxalin and eosin. Tissues were examined by routine light microscopy on an Axioscop Microscope (Carl Zeiss Micro Imaging, Inc. Thornwood, N.Y.). Digital light microscopic images were taken on Zeiss Axioskop2 Plus microscope, AxoCam HR Camera, and AxioVision 5.05.10 imaging software (Carl Zeiss Micro Imaging, Inc. Thornwood, N.Y.).

The results of this experimental example are now described.

The presence of Wnt3a and bFGF alone in standard DMEM/F12 medium cannot support hESC growth in the absence of a feeder layer and serum (Table 1). The addition of insulin, transferrin, albumin and April/BAFF in the medium with Wnt3a and bFGF was found to support hESC proliferation for more than 10 passages. However, the cells grown in this medium divide and die at about the same rate, which makes the cell culture difficult to expand. To further optimize the hESC culture conditions, therefore, a variety of different components were tested. The addition of albumin was found to allow hESC expansion. The further addition of chemically-defined cholesterol to the medium was found to improve hESC expansion (Table 1). Thus, the final cocktail, called HESCO, for proliferation of hESC in culture, contains Wnt3a, bFGF, insulin, transferrin, April/BAFF, cholesterol, and albumin. Basal medium containing HESCO can actively support hESC self-renewal. Notably, hESCs grown in feeder cell-conditioned medium can be directly shifted to HESCO medium and vice versa without the need for gradual adaptation steps in the culture. This result suggests that the signals supporting the hESC growth are similar in these two conditions.

TABLE 1

Summary of cell growth with different cytokine cocktail combinations

| Components* | | | | |
|---|---|---|---|---|
| April/BAFF | - | ✓ | ✓ | - |
| bFGF | ✓ | ✓ | ✓ | - |
| Wnt3a | ✓ | ✓ | ✓ | - |
| insulin | - | ✓ | ✓ | - |
| transferrin | - | ✓ | ✓ | - |
| albumin | - | ✓ | ✓ | - |
| cholesterol | - | - | ✓ | - |
| conditioned medium | - | - | - | ✓ |
| Growth** | - | + | ++ | ++ |

*All cells were cultured on Matrigel ™-coated tissue culture plates.
**The relative amounts of cells with undifferentiated morphology after passage 10 are indicated in the row labeled "Growth."

Several matrices in combination with the HESCO culture medium were also tested. Among them, fibronectin consistently supported hESC growth (Table 2). The presence of collagen along with fibronectin further improved the survival of hESCs (Table 2).

TABLE 2

Summary of cell growth using different coating matrix

| Matrix | | | | | |
|---|---|---|---|---|---|
| fibronectin | ✓ | | | ✓ | |
| collagen | | ✓ | | ✓ | |
| laminin | | | ✓ | | |
| matrigel | | | | | ✓ |
| Growth* | +++ | ++ | + | ++++ | ++++ |

*The relative amounts of cells with undifferentiated morphology after passage 3 are indicated in the row labeled "Growth."

In order to define the minimal components for hESC growth, fibronectin in the absence of collagen was used as the matrix in experimental examples described below. The final hESC growth conditions using HESCO culture medium and fibronectin were therefore defined and contained only recombinant, chemically synthesized or human-source purified components.

Experimental Example 2 hESCs Cultured in HESCO Exhibit Normal Cell Morphologies

Figure 2B:
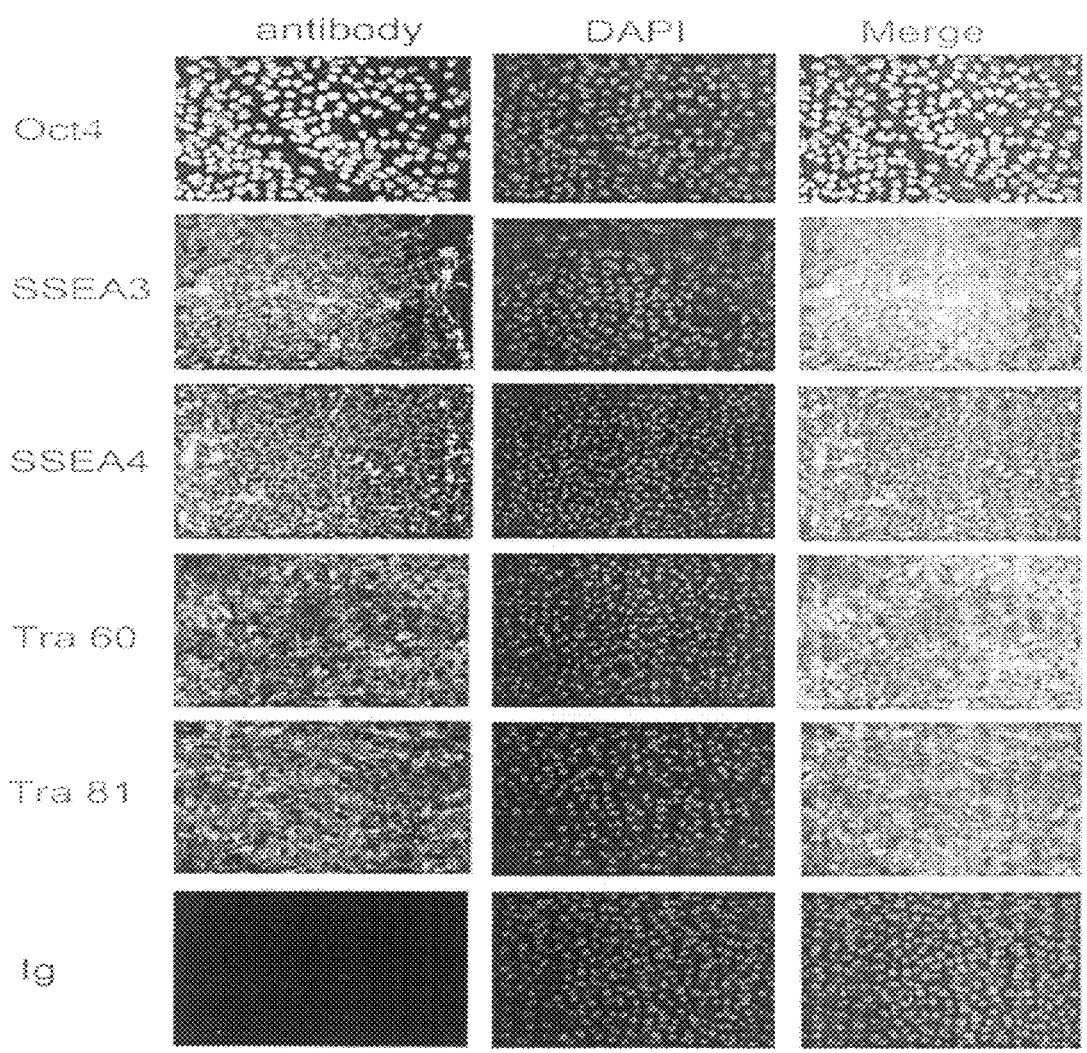

To determine whether hESCs grown in HESCO culture medium were maintained in an undifferentiated state, a variety of tests were used. The morphology of two hESC lines, H9 and BG01, cultured in HESCO culture medium or conditioned medium for greater than 2 months (8 passages) was examined. Fibronectin and matrigel from at least 6 different lots were tested and gave consistent results. Unlike the elongated cells observed in conditioned medium, hESCs cultured in HESCO were more condensed and had a high nucleus to cytoplasm ratio similar to cells cultured on feeder cells (FIG. 1). Importantly, hESCs cultured in HESCO did not have the differentiated cells surrounding the hESC colonies (FIGS. 1 and 2). This result is in contrast to most feeder-free culture conditions currently used (Xu et al., 2005, Stem Cells 23: 315-23; Li et al., 2005, Biotechnol Bioeng 91: 688-98). As negative controls, species-matched IgG and IgM were used to stain hESCs cultured in HESCO culture medium, and signal was not detected (FIG. 2B). These results indicate that the exogenous factors in the HESCO medium are sufficient for hESC growth in an undifferentiated stage for more than 8 passages.

Experimental Example 3

HESCS Cultured in HESCO Express Stem Cell Markers

HESCs express stem cell markers that distinguish them from differentiated cells. To confirm that hESCs grown in the HESCO for 2 months are undifferentiated, alkaline phosphatase activities were measured using an in situ assay (Pease et al., 1990, Dev Biol 141: 344-52). Both H9 and BG01 cells had alkaline phosphatase activities comparable to the cells grown in conditioned medium or on feeder cells (FIG. 2A). The undifferentiated state of hESCs was further demonstrated by the expression of the stem cell markers Oct4, SSEA3, SSEA4, TRA-1-60, and TRA-1-81 using indirect immunofluoresence assays. In both H9 and BG01 cell lines, more than 95% of cells cultivated in HESCO stained positive for each of the stem cell markers (FIG. 2B). In each case, expression of the stem cell marker revealed that the hESC colonies were not surrounded by differentiated cells (FIG. 2). As negative controls, species-matched IgGs and IgM were used to stain hESCs cultured in HESCO, and signal was not detected (FIG. 2B). These results indicate that the exogenous factors in the HESCO were sufficient for hESC growth in an undifferentiated state for more than 8 passages.

Experimental Example 4

Karyotyping of HESCs Cultured in HESCO hESCs cultured in vitro can lose their genetic integrity through passaging (Ludwig et al., 2006, Nat Biotechnol. 24: 185-187; Brimble et al., 2004, Stem Cells Dev 13: 585-97; Draper et al., 2004, Nat Biotechnol 22: 53-4). For example, BG01 cells cultured in conditioned medium occasionally develop trisomy 12 or 17. To examine the genetic stability of hESCs in HESCO, H9 cells cultured in HESCO for 4, 11, and 23 passages (1-6 months), and BG01 cells cultured for 8 passages (2 months) were karyotyped. In each case, the karyotype was normal (FIG. 3). No major translocations or other chromosomal changes were observed during this period. Thus, hESCs cultured in HESCO maintain their genomic integrity.

Experimental Example 5

Figure 4:
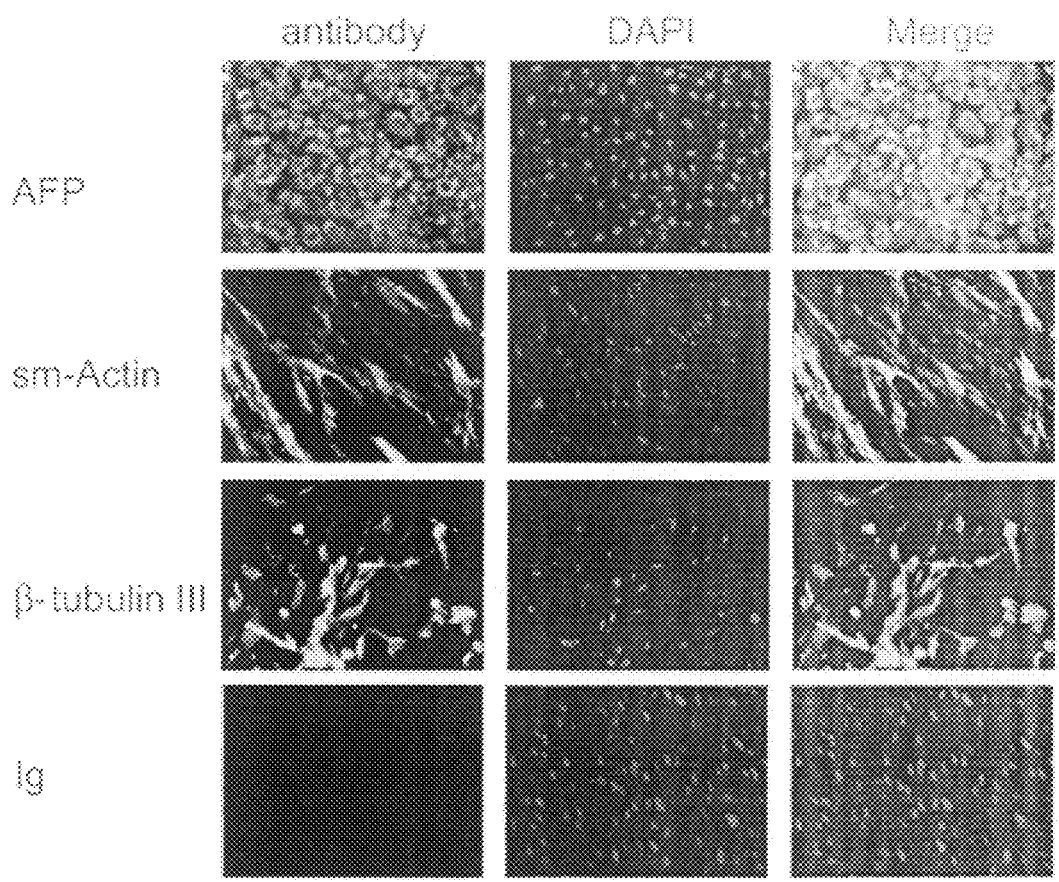
FIG. 4 is a series of images illustrating the pluripotency of hESCs cultured in HESCO medium in vitro. The left column of images (Antibody) depicts cells derived from H9 cells cultured in vitro and induced to form embryoid bodies. The derived cells were stained with an isotyped-matched immunoglobulin control (Ig) and different differentiation markers: AFP (alpha feto protein), sm-Actin (muscle tubulin), or β-tubulin III. The middle column of images (DAPI) depicts nuclei stained with DAPI. The right column of images (Merge) depicts the overlay of FITC antibody staining and DAPI signals. Original magnification: ×200.

HESCs Cultured in HESCO Are Pluripotent hESCs are pluripotent cells that can differentiate into the three major cell lineages, endodermal, ectodermal, and mesodermal (8, 34). To confirm that hESCs cultured in HESCO still maintain their pluripotency in vitro, embryoid body formation and differentiation assays in H9 and BG01 cells were performed. Three passages of H9 cells (passages 5, 10, 24) and one passage of BG01 cells (passage 9) were tested. After dispersing the cells by enzymatic digestion, hESCs formed embryoid bodies in suspension with high efficiency in both cell lines. Subsequently, the embryoid bodies continued to differentiate on gelatin-coated plates for at least 10 days. Expression of endoderm, mesoderm, and ectoderm-specific markers in the embryoid body-derived cells was evaluated using immunofluoresence analysis of alpha-feto protein, muscle tubulin, and β tubulin III, respectively. In both hESC lines and in all passages tested, the embryoid body-derived cells contained cells from three different lineages (FIG. 4). Immunofluorescence signal was not evident in the immunoglobulin control (FIG. 4). Hence, the HESCO medium was sufficient to maintain the pluripotency of hESCs.

Figure 5:
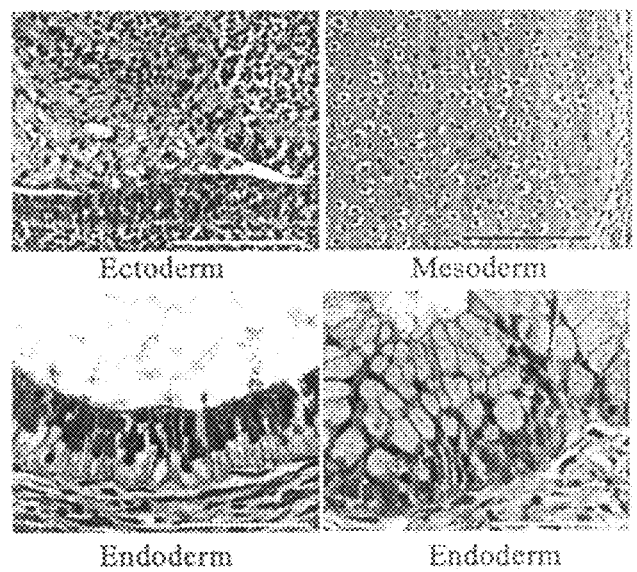
FIG. 5 is a series of images depicting sections of teratomas stained with hematoxylin-eosin to analyze the in vivo pluripotency of hESCs cultured in HESCO medium. H9 cells were subcutaneously injected into the SCID mice. Sections of the resulting teratomas were stained with hematoxylin-eosin. Scale bar: 100 μm (top two images) and 50 μm (bottom two images).

To examine the in vivo pluripotency of hESCs grown in HESCO, their ability to form teratomas was assessed. H9 and BG01 hESCs cultured in HESCO for 8 passages were injected subcutaneously into SCID mice. Teratomas were formed, and they contained multiple cell types from each of the major cell lineages, including neuroepithelium (ectoderm), cartilage (mesoderm), ciliated epithelium (endoderm), and mucus-producing epithelium (endoderm) (FIG. 5). Thus, the cells cultured in HESCO maintain their pluripotency in vivo.

Experimental Example 6

Varying Concentration of Wnt3a and bFGF

H9 and BG01 are cultured in HESCO medium comprising insulin (160 ug/ml), transferrin (88 ug/ml, Wnt3a (100 ng/ml), April or BAFF (100 ng/ml), albumin (2.5 mg/ml), and cholesterol lipid supplement (2.5×; Invitrogen) in DMEM/F12, with varying concentrations of Wnt3a and bFGF. A fibronectin matrix is used. Wnt3a is varied from 100 ng/ml to 0 ng/ml, while bFGF is inversely varied from 16 ng/ml to 100 ng/ml, as shown in Table 3. At 10 passages, cell growth is about comparable among the three conditions.

TABLE 3

| Component | | | |
|---|---|---|---|
| Wnt3a | 100 ng/ml | 50 ng/ml | 0 ng/ml |
| bFGF | 16 ng/ml | 50 ng/ml | 100 ng/ml |
| Growth* | +++ | +++ | +++ |

The undifferentiated state of the hESCs after 2 months of culture is determined by alkaline phosphatase activity and expression of stem cell markers (Oct4, SSEA3, SSEA4, TRA-1-60, and TRA-1-81) as described above using indirect immunofluoresence assays. In both H9 and BG01 cell lines, more than 95% of cells cultivated in the three different conditions stain positive for each of the stem cell markers. In each case, expression of the stem cell marker reveals that the hESC colonies are not surrounded by differentiated cells. Karyotyping at 4 passages, 8 passages and 20 passages is normal. Embryoid body formation and differentiation assays in H9 and BG01 cells is performed and demonstrates that the cells in each of the three conditions are pluripotent. Teratomas are formed using cells at 8 passages. Examination shows that teratomas contained multiple cell types from each of the major cell lineages.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A culture medium for the maintenance and proliferation of substantially undifferentiated stem cells, wherein said culture medium comprises a basal medium, a protein comprising a member of the tumor necrosis factor (TNF) family, a protein comprising a member of the Wnt family, a protein comprising insulin, a protein comprising transferrin and a protein comprising fibroblast growth factor (FGF), wherein a population of substantially undifferentiated stem cells cultured in said culture medium proliferates while maintaining a substantially undifferentiated state for at least about 4 passages.

2. The culture medium of claim 1, wherein said protein comprising a TNF member is selected from the group consisting of APRIL, an APRIL substitute, BAFF, a BAFF substitute and combinations thereof.

3. The culture medium of claim 1, wherein said protein comprising a member of the Wnt family is Wnt3a or a Wnt3a substitute.

4. The culture medium of claim 1, wherein said basal medium is selected from the group consisting of DMEM and DMEM/F12, further wherein said insulin is present at about 160 ug/ml, wherein said transferrin is present at about 88 ug/ml, wherein said member of the Wnt family is present at about 100 ng/ml, and wherein said member of the TNF family is present at about 100 ng/ml.

5. The culture medium of claim 1, further comprising a protein comprising albumin.

6. The culture medium of claim 1, further comprising cholesterol.

7. The culture medium of claim 6, wherein said cholesterol is chemically-defined cholesterol.

8. The culture medium of claim 1, wherein said protein comprising FGF is basic fibroblast growth factor (bFGF).

9. The culture medium of claim 1, wherein any of said proteins are recombinantly synthesized, chemically synthesized or isolated from a human biological sample.

10. The culture medium of claim 1, wherein any of said proteins are recombinantly synthesized and/or chemically synthesized.

11. The culture medium of claim 1, wherein said medium is essentially free of animal serum.

* * * * *

UNITED STATES PATENT AND TRADEMARK OFFICE
CERTIFICATE OF CORRECTION

| | | |
|---|---|---|
| PATENT NO. | : 9,101,590 B2 | Page 1 of 1 |
| APPLICATION NO. | : 11/989363 | |
| DATED | : August 11, 2015 | |
| INVENTOR(S) | : Michael P. Snyder and Joyce J. Lu | |

It is certified that error appears in the above-identified patent and that said Letters Patent is hereby corrected as shown below:

In the Specification

Replace Lines 15-21 of Column 1 with the following:
-- STATEMENT REGARDING FEDERALLY SPONSORED RESEARCH OR DEVELOPMENT
This invention was made with government support under HG002357 awarded by National Institutes of Health. The government has certain rights in the invention. --

Signed and Sealed this
Twenty-ninth Day of August, 2023

*Katherine Kelly Vidal*

Katherine Kelly Vidal
*Director of the United States Patent and Trademark Office*